United States Patent
Okada

(10) Patent No.: US 6,802,809 B2
(45) Date of Patent: Oct. 12, 2004

(54) ENDOSCOPE

(75) Inventor: Yuta Okada, Hachioji (JP)

(73) Assignee: Olympus Corporation, Tokyo (JP)

( * ) Notice: Subject to any disclaimer, the term of this patent is extended or adjusted under 35 U.S.C. 154(b) by 145 days.

(21) Appl. No.: 10/184,550

(22) Filed: Jun. 28, 2002

(65) Prior Publication Data

US 2003/0018237 A1 Jan. 23, 2003

(30) Foreign Application Priority Data

Jun. 29, 2001 (JP) .................................. 2001-199234

(51) Int. Cl.$^7$ ............................................. A61B 1/00
(52) U.S. Cl. ..................................... 600/146; 600/152
(58) Field of Search ............................... 600/107, 118, 600/102, 103, 110, 112, 130, 131, 126, 146, 152

(56) References Cited

U.S. PATENT DOCUMENTS

| | | | | |
|---|---|---|---|---|
| 5,609,560 A | * | 3/1997 | Ichikawa et al. | ............ 600/101 |
| 6,468,203 B2 | * | 10/2002 | Belson | ......................... 600/146 |
| 6,602,185 B1 | * | 8/2003 | Uchikubo | ................... 600/118 |
| 6,612,981 B2 | * | 9/2003 | Onishi et al. | ................ 600/118 |
| 2002/0198439 A1 | * | 12/2002 | Mizuno | ....................... 600/109 |

FOREIGN PATENT DOCUMENTS

| | | |
|---|---|---|
| JP | 56-5629 | 1/1981 |
| JP | 57-57521 | 4/1982 |
| JP | 63-182701 | 11/1988 |
| JP | 1-175828 | 7/1989 |
| JP | 2-126603 | 10/1990 |
| JP | 7-184844 | 7/1995 |
| JP | 8-206162 | 8/1996 |
| JP | 2000-217827 | 8/2000 |

* cited by examiner

Primary Examiner—Beverly M. Flanagan
(74) Attorney, Agent, or Firm—Scully, Scott, Murphy & Presser

(57) ABSTRACT

A cylindrical proximal unit is disposed at the proximal end of an elongated insertion unit that has a CCD incorporated in a distal part thereof and that has a bending section. A light source unit, a circuit for producing a CCD driving signal in response to a signal received from an external unit by radio, and a motor unit for electrically driving the bending section are incorporated in the proximal unit. Thus, a light guide cable need not be led out of the proximal unit. This leads to easy operation. Moreover, by manipulating an operation unit separated from an endoscope, a motor included in the motor unit is driven by radio via a scope interface unit.

22 Claims, 13 Drawing Sheets

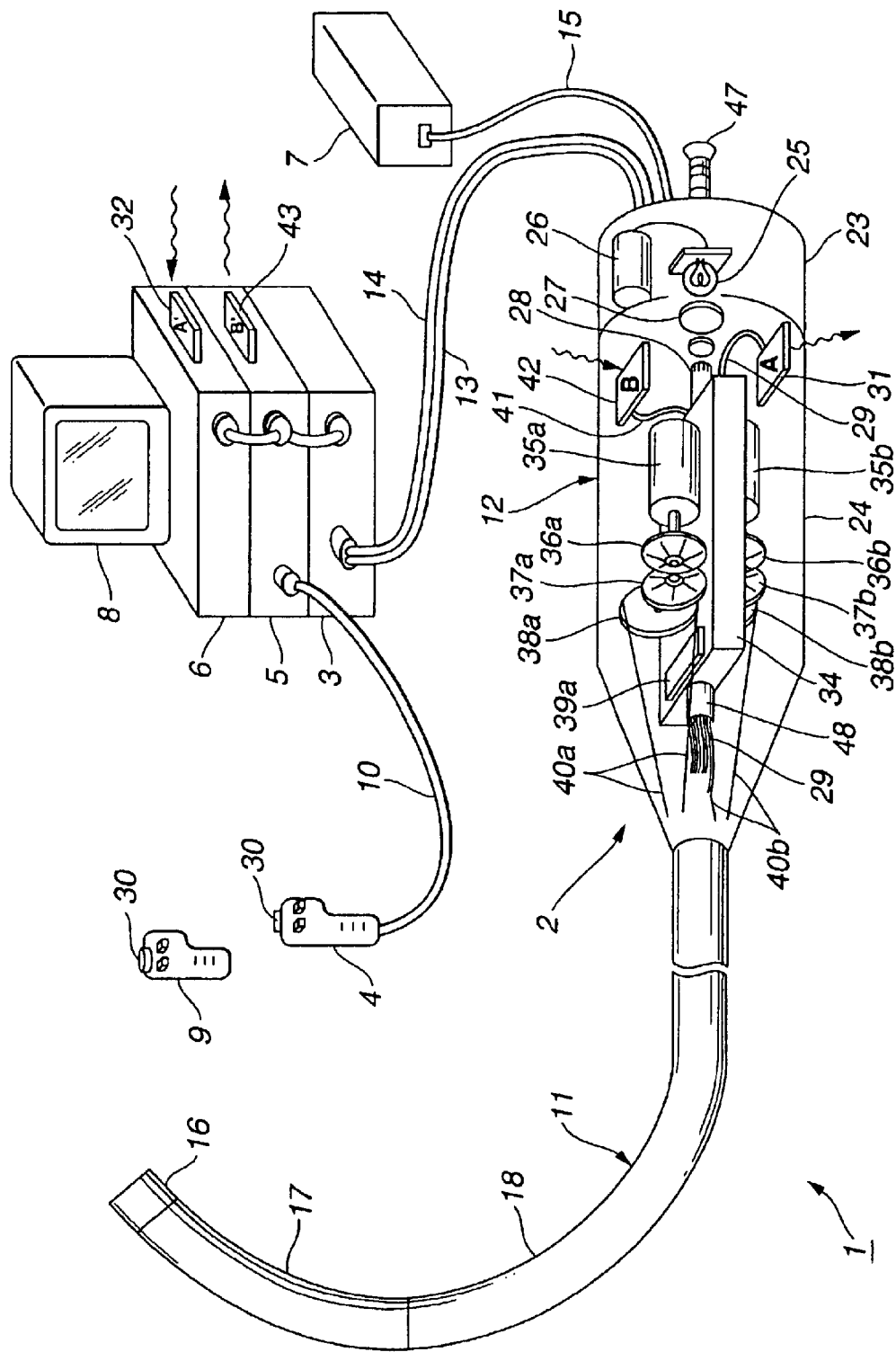

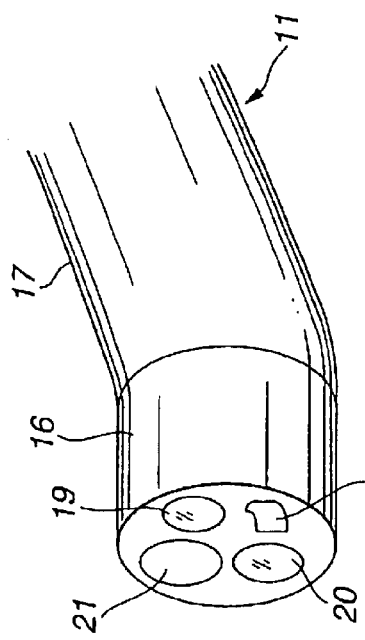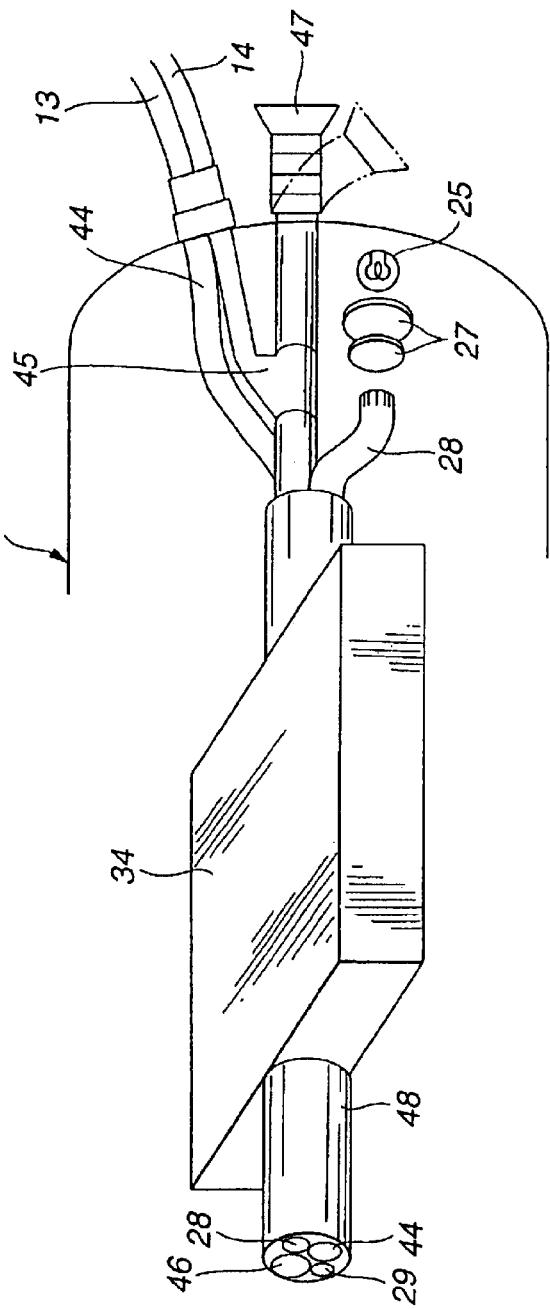

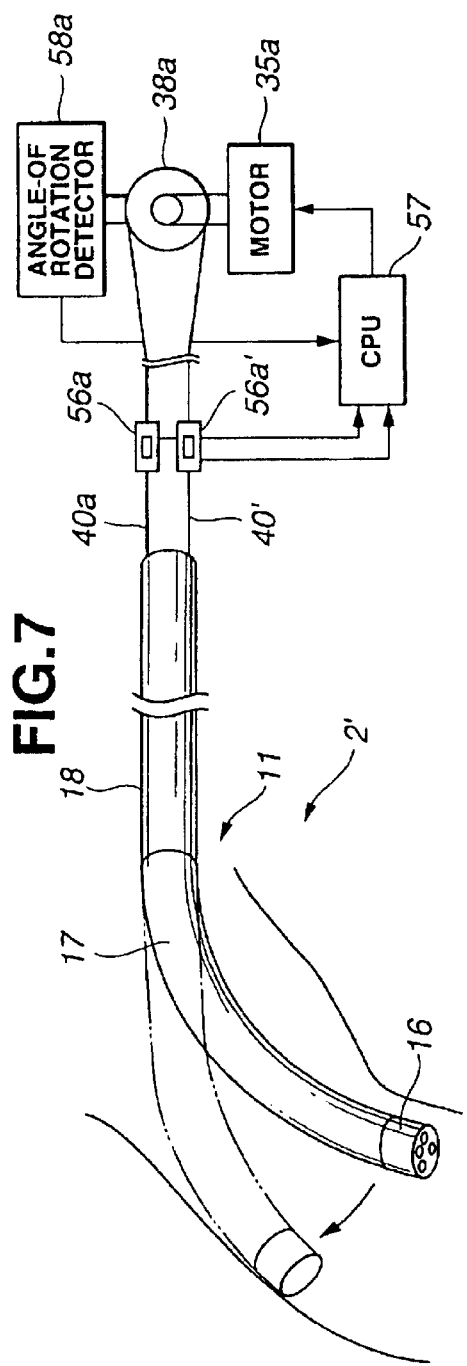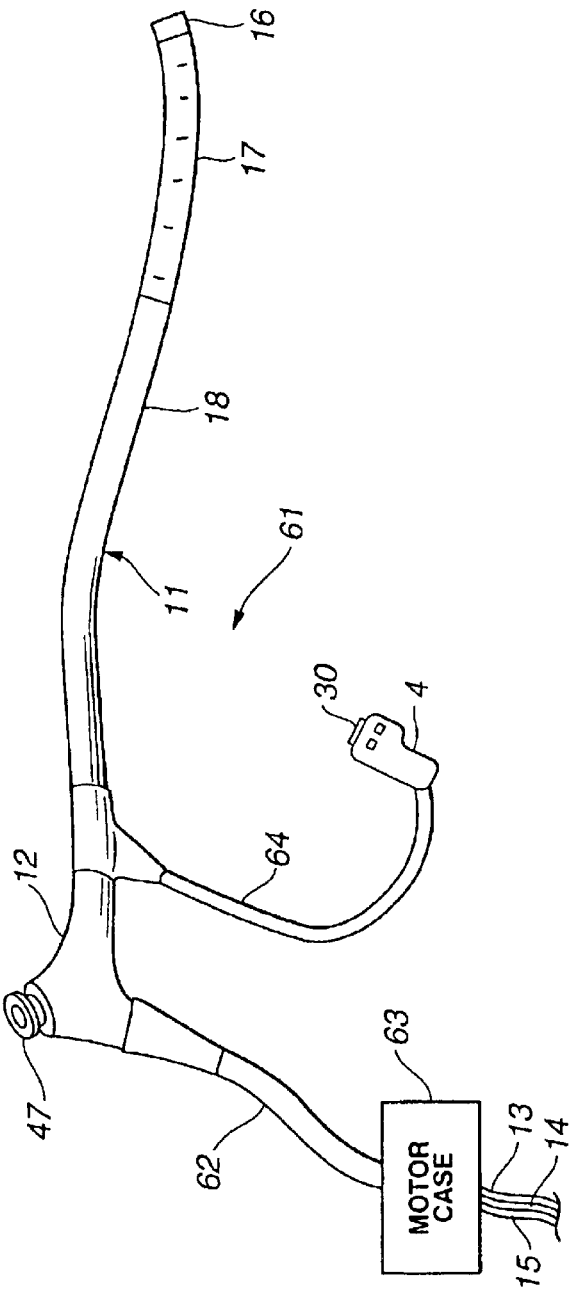

ENDOSCOPE

This application claims the benefit of Japanese Application No. 2001-199234 filed on Jun. 29, 2001, the contents of which are incorporated by this reference.

BACKGROUND OF THE INVENTION

Field of the Invention and Description of the Related Art

The present invention relates to an endoscope whose bending section is electrically bent using a motor.

In endoscopes whose insertion units are soft, the insertion unit is provided with a bending section so that the insertion unit can be inserted smoothly into a tortuous body cavity.

FIG. 1 shows an endoscope system 121 in accordance with a related art. The endoscope system 121 consists mainly of: an endoscope 122 in which an imaging device is incorporated; a light source apparatus 123 that supplies illumination light to the endoscope 122; a video processor 124 that processes an image signal produced by the endoscope 122; a color monitor 125 on which a view image is displayed according to a video signal transferred from the video processor 124; a VTR deck 126 and a video disk 127 that are used to record view images; and a video printer 128 that prints view images.

The endoscope 122 includes an elongated soft insertion unit 129, an operation unit 130 disposed at the rear end of the insertion unit 129 and held by an operator in order to operate the endoscope, and a universal cord 131 led out of the operation unit 130. A light guide connector that is included in a connector 132 fixed to the terminal of the universal cord 131 is coupled to the light source apparatus 123 so that it can be decoupled freely.

Moreover, a connector 133a fixed to the terminal of a signal cable 133 spliced to an electric connector included in the connector 132 is coupled to the video processor 124 so that it can be decoupled freely.

The insertion unit 129 includes a distal part 134 in which an illumination optical system and an observation optical system are placed and which is formed with a hard member, a bending section 135 capable of freely bending vertically, and a pliable flexible (soft) part 136 having flexibility (being soft). An angling knob 137 formed on the operation unit 130 is manipulated in order to bend the bending section 135.

Illumination light emanating from a lamp 138 included in the light source apparatus 123 travels through a condenser lens 139 and converges on the end surface of the light guide connector. The light is then propagated to the distal part 134 of the insertion unit 129 over a light guide that lies through the universal cord 131 and endoscope 122 alike, and irradiated to an object such as a lesion through an illumination window. A treatment appliance insertion port 140 is bored near the front end of the operation unit 130.

In the endoscope 122 of the related art, the bending section 135 and the angling knob 137 formed on the operation unit 130 are connected to each other using a traction member realized with angling wires that are not shown. An operator turns the angling knob 137 to operate the endoscope 122. The operation unit 130 must therefore be connected on a fixed basis to a hand-held unit 130a proximal to the insertion unit 129. The operator must hold the hand-held unit 130a integrated with the operation unit 130 all the time.

Furthermore, the universal cord 131 is led out of the operation unit 130. Over the universal cord 131, the endoscope is connected to the video processor 124 and light source apparatus 123 that are disposed outside the endoscope. Incidentally, an operator may change the way of holding the hand-held unit 130a so as to manipulate the angling knob 137 or press various switches, or may advance, withdraw, or twist the operation unit 130 so as to thrust, pull, or twist the insertion unit 129. In this case, the universal cord 131 led out of the operation unit 130 is moved or twisted accordingly. This obstructs an operator.

Moreover, fragile built-in components including an image transmission cable and a light guide are run through the universal cord 131. In order to protect the built-in components, the armor of the universal cord 131 must be formed with a member that is as thick as the insertion unit 129. When the operation unit 130 is twisted, the universal cord 131 must also be twisted as mentioned above. An operator must therefore apply a large torsion as a whole.

As mentioned above, in the endoscope of the related art, the insertion unit and operation unit are integrated with each other. The universal cord over which the endoscope is connected to the light source apparatus or video processor and which protects a plurality of built-in components is fixed to the operation unit. When the operation unit is moved in order to manipulate the insertion unit, the universal cord is moved accordingly to obstruct an operator. This poses a problem.

Furthermore, there is a motor-driven endoscope in which a traction member coupled to a bending section is pulled using a motor and the bending section is thus bent. Herein, the traction member is passed through a universal cord, and then pulled by actuating the motor. When the universal cord is twisted, the friction of the traction member increases. Namely, in order to bend the bending section, a large load must be cleared. This is a drawback of the motor-driven endoscope.

In addition, for example, Japanese Unexamined Utility Model Application Publication No. 1-159801 has disclosed a columnar control apparatus for endoscopes. Moreover, Japanese Unexamined Patent Application Publication No. 2000-217827 has disclosed an apparatus having a power supply driving battery made movable along side rails on an operating table.

OBJECTS AND SUMMARY OF THE INVENTION

Accordingly, an object of the present invention is to provide an endoscope with excellent maneuverability whose insertion unit can be inserted easily.

Another object of the present invention is to provide an endoscope with excellent maneuverability that permits easy endoscopic examination.

According to the present invention, an endoscope consists mainly of:

a main body including an insertion unit that has a bending mechanism and that includes a bending section capable of bending freely, and a proximal unit disposed proximally to the insertion unit;

an objective optical system mounted in an imaging window formed in a distal part of the insertion unit, and a solid-state imaging device disposed at the position of the image plane of the objective optical system;

an actuator included in the proximal unit and used to operate the bending mechanism so as to bend the bending section;

a light source unit that is included in the proximal unit and that generates illumination light with which an object to be imaged by the solid-state imaging device is illuminated an object;

a communication device that is included in the proximal unit and that transmits an image signal produced by the solid-state imaging device to an external signal processing unit by radio; and an operation unit formed separately from the main body and used to operate the actuator.

In order to insert the insertion unit or in order to angle the insertion unit for insertion by handling the operation unit, the endoscope is connected to a light source apparatus or a video processor over a universal cord. However, the above configuration obviates the necessity of the universal cord and facilitates inserting work.

BRIEF DESCRIPTION OF THE DRAWINGS

FIG. 2A to FIG. 6E are concerned with a first embodiment of the present invention;

FIG. 2A shows the overall configuration of a video endoscope system including the first embodiment;

FIG. 3 is a perspective view showing the distal part of an insertion unit in enlargement;

FIG. 4 shows part of a proximal unit in enlargement;

FIG. 5 is a perspective view showing an operating table to which an endoscope holder is fixed;

FIG. 6E is an explanatory diagram showing the center of gravity of the proximal unit and a direction of angling;

FIG. 7 schematically shows the components of a video endoscope in accordance with a second embodiment of the present invention:

FIG. 8 schematically shows the components of a video endoscope in accordance with a third embodiment of the present invention;

DESCRIPTION OF THE PREFERRED EMBODIMENTS

Figure 1:
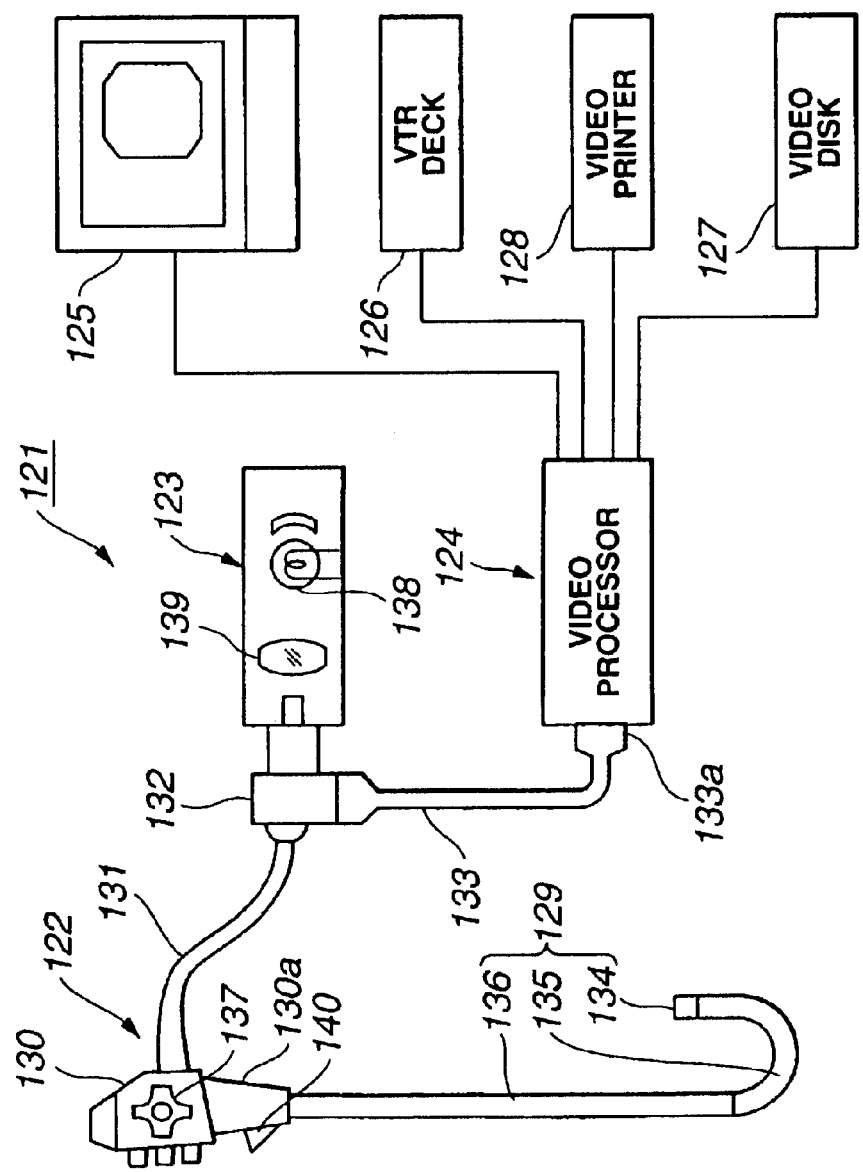
FIG. 1 shows the overall configuration of an endoscope system including an endoscope in accordance with a related art.

Embodiments of the present invention will be described with reference to the drawings below.

First Embodiment

Referring to FIG. 2A to FIG. 6E, a first embodiment of the present invention will be described below.

An electrically bendable video endoscope system 1 shown in FIG. 2A and FIG. 2B consists mainly of: an electrically bendable video endoscope (hereinafter, simply, a video endoscope or an endoscope) 2; an electromagnetic valve unit 3 to which the video endoscope 2 is connected; an operation unit 4 used to angle the endoscope or give an instruction; a scope interface unit 5 connected to the operation unit 4; a video processor 6 that is connected to the scope interface unit 5 and that processes a signal produced by an imaging device incorporated in the video endoscope 2; a driving power supply unit 7 that is connected to the video endoscope 2 and that supplies driving power; and a monitor 8 that is connected to the video processor 6 and on which an endoscopic image picked up by the imaging device is displayed.

The operation unit 4 used to angle the endoscope or instruct aeration, perfusion, or suction is connected to the scope interface unit 5 over an operation unit connection cable 10.

The scope interface unit 5 that processes a received signal, for example, converts a received signal into a control signal used to control the video endoscope 2 in response to an operational instruction sent from the operation unit 4 is connected to the video processor 6 over a connection cable. The scope interface unit 5 is also connected to the electromagnetic valve unit 3.

The video endoscope 2 includes an elongated insertion unit 11 that is inserted into a body cavity or the like, and a proximal unit 12 disposed at the rear end of the insertion unit 11. An aeration/perfusion tube 13 and a suction tube 14 led out of the rear end of the proximal unit 12 are routed to the electromagnetic valve unit 3. A power cable 15 led out of the rear end of the proximal unit 12 is routed to the driving power supply unit 7.

The insertion unit 11 consists of a distal part 16 disposed distally, a bending section (bending tube) 17 disposed at the rear end of the distal part 16 and capable of freely bending, and a flexible tube 18 extending from the rear end of the bending section 17 to the front end of the proximal unit 12 and having flexibility.

Figure 2B:
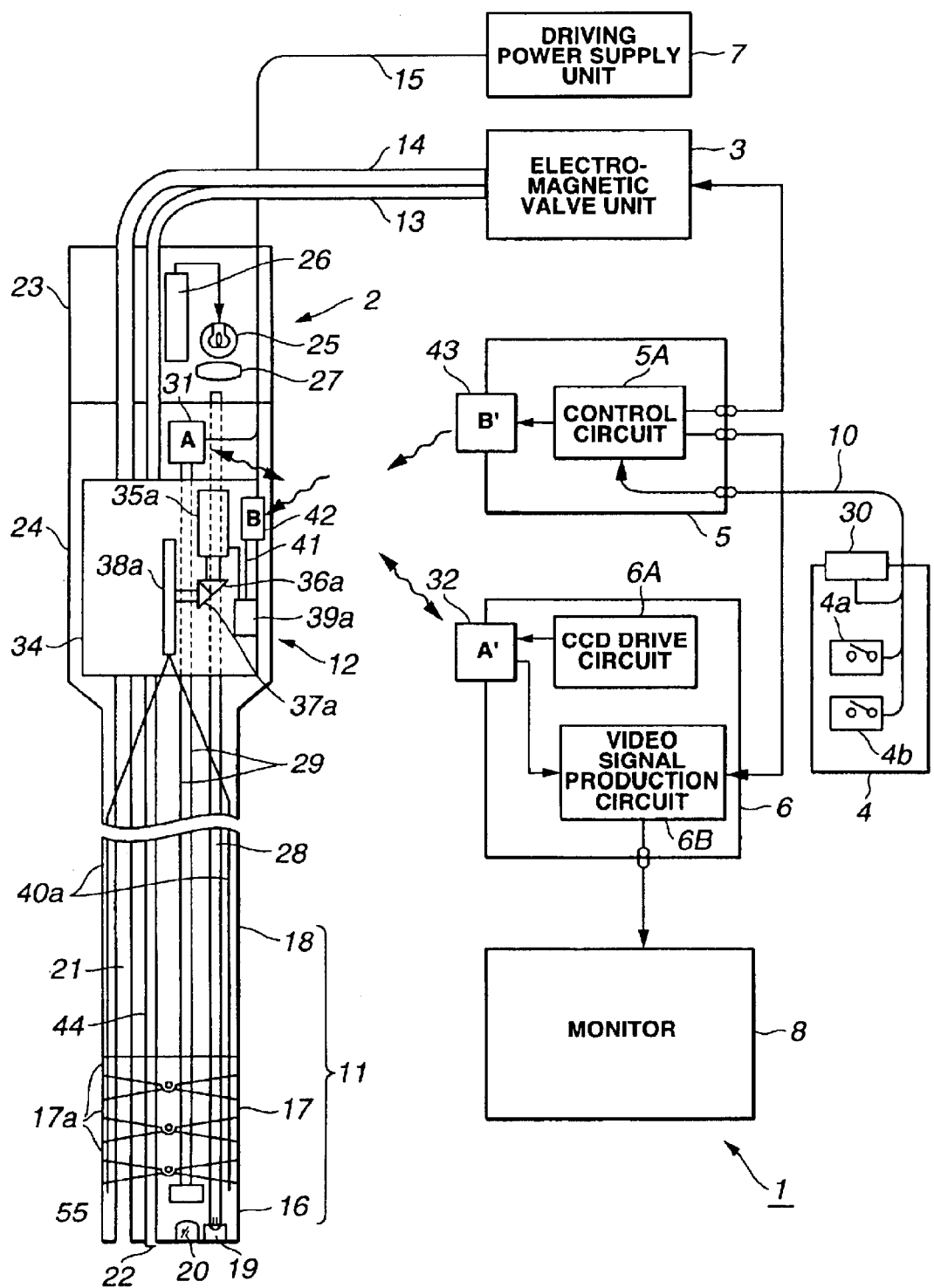
FIG. 2B schematically shows the components of the video endoscope system.

The distal part 16 includes, as shown in FIG. 2B and FIG. 3, an illumination lens 19, an observation lens (objective) 20, a treatment appliance insertion hole 21, and a cleansing nozzle 22 used to cleanse the observation lens 20.

The proximal unit 12 has, as shown in FIG. 2A and FIG. 2B, for example, a light source unit 23 disposed in the rear part thereof, and has a motor unit 24 (as an electric actuator) disposed in the front part thereof. A lamp 25 incorporated in the light source unit 23 is lit with a battery 26. Light emanating from the lamp 25 is converged by a condenser lens 27 and irradiated to the rear end of a light guide 28.

The light incident on the rear end of the light guide 28 is propagated to the front part of the light guide 28. The light guide 28 is routed to the distal part 16 of the insertion unit 11 through the motor unit 24. The light is then passed through the illumination lens 19 opposed to a distal screen fixed as the distal surface of the distal part 16, and radiated to an intracavitary lesion located in front of the illumination lens 19 through the distal screen. Consequently, an object is illuminated.

An optical image of the illuminated object is formed on the image plane of the observation lens 20. A solid-state imaging device, for example, a CCD 55 (see FIG. 2B) is located at the position of the image plane. The CCD 55 is connected to a communication device (A in FIG. 2A and FIG. 1B) 31 incorporated in the proximal unit 12 over a driving and image transmitting cable 29 that lies through the insertion unit 11.

The communication device 31 is connected to a communication device 32 (A' in FIG. 2A and FIG. 2B) included in the video processor 6 so that the communication devices can communicate with each other by radio. In other words, the communication devices can transfer signals to or from each other.

To be more specific, as shown in FIG. 2B, the video processor 6 has a CCD drive circuit 6A and a video signal production circuit 6B incorporated therein. The CCD drive circuit 6A and video signal production circuit 6B are connected to the communication device 32.

The communication device 32 modulates a CCD driving signal with which the CCD is driven, and transmits a resultant radio-frequency (RF) signal. The communication device 31 in the proximal unit 12 receives the signal, demodulates the CCD driving signal, and transmits the CCD driving signal over the driving and image transmitting cable 29. Consequently, the CCD 55 is driven. A signal charge resulting from photoelectric conversion performed by the CCD 55 is then read. The communication device 31 transmits the signal charge to the communication device 32 included in the video processor 6.

Incidentally, when a circuit for producing a CCD driving signal is included in the proximal unit 12, the communication device 31 included in the proximal unit 12 may have only the ability to transmit a signal, which results from photoelectric conversion performed by the CCD, to the communication device 32 included in the video processor 6 by radio.

In the video processor 6, the video signal production circuit 6B processes the signal received by the communication device 32, produces a standard video signal, and transfers the video signal to the monitor 8. An object image picked up by the CCD 55 is then displayed on the display surface of the monitor 8.

Each of pairs of motors 35a and 35b, gears 36a and 36b, gears 37a and 37b, pulleys 38a and 38b, and motor control circuits 39a and 39b (FIG. 2A shows one of the motor control circuits, that is, the motor control circuit 39a) is mounted symmetrically to each other on two sides (the face and back) of a base 34 in the motor unit 24.

Moreover, angling wires 40a and angling wires 40b are wound about the pulleys 38a and 38b respectively. The motor 35a serves as a driving motor for angling in upward and downward directions, while the motor 35b serves as a driving motor for angling in rightward and leftward directions.

To be more specific, the angling wires 40a having the rear parts thereof wound about the pulley 38a that is rotated by the motor 35a have the distal ends thereof passed through the flexible tube 18 and a plurality of bending pieces 17a constituting the bending section 17. The distal ends are then fixed to the points on the rear end wall of the distal part 16 lying in the upward and downward directions.

The distal ends of the angling wires 40a may be fixed to, for example, the points on the internal wall of the leading bending piece 17a which lie in the upward and downward directions, in place of the distal part 16.

The angling wires 40b having the rear parts thereof wound about the pulley 38b that is rotated by the other motor 35b have the distal ends thereof fixed to the points on the wall of the distal part 16 or of the leading bending piece which lie in the rightward and leftward directions.

The rotation of a motor 35i (i denotes a or b) that is controlled by a motor control circuit 39i is conveyed to a pulley 38i by way of the gears 36i and 37i. This causes the pulley 38i to rotate. Consequently, one pair of angling wires 40i wound about the pulleys 38i is pulled, the other pair of angling wires is loosened. The bending section 17 bends in the direction of the pulled angling wire.

Driving power is delivered from the external driving power supply unit 7 to the motors 35a and 35b and motor control circuits 39a and 39b respectively. The motors 35a and 35b can be rotated in a forward direction and an opposite direction by means of the motor control circuits 39a and 39b.

As mentioned above, the angling wires 40a passed through the upward and downward portions of the bending section 17 and the angling wires 40b passed through the rightward and leftward portions thereof have the directions of rotation thereof controlled by the two motors 35a and 35b. Thus, the bending section can be bent in the four directions of the upward and downward directions and the rightward and leftward directions.

The motor control circuits 39a and 39b are connected to a communication device 42 (B in FIG. 2A and FIG. 2B) over a control cable 41.

The communication device 42 can communicate with a communication device 43 (B' in FIG. 2A and FIG. 2B) included in the scope interface unit 5 by radio. For example, based on an instruction signal sent by radio from the communication device 43, the motors 35a and 35b are driven via the motor control circuits 39a and 39b.

In other words, an operator manipulates the angling member 30 of the operation unit 4. Consequently, an instruction signal (command signal) is produced responsively to the manipulation, processed by a control circuit 5A included in the scope interface unit 5, and transmitted by ratio from the communication device 43 to the communication device 42. The signal received by the communication device 42 is demodulated and transferred to the motor control circuits 39a and 39b. The motor control circuits 39a and 39b rotate the motor 35a or 35b in a forward or opposite direction in response to the instruction signal. Consequently, the bending section 17 is driven to bend.

A plurality of pumps that is not shown is incorporated in the electromagnetic valve unit 3. The pumps are actuated in response to an instruction signal received from the operation unit 4 via the scope interface unit 5. The video endoscope 2 can perform aeration, perfusion, or suction by way of the aeration/perfusion tube 13 and suction tube 14 whose rear ends are coupled to the electromagnetic valve unit 3.

FIG. 4 is an enlarged view showing part of the proximal unit 12.

In the video endoscope 2, the aeration/perfusion tube 13 is joined to an aeration/perfusion channel 44, and the suction tube 14 is joined to a treatment appliance passage 46 via a bifurcation member 45. The aeration/perfusion channel 44 is joined to the cleansing nozzle 22 in the distal part 16. A cleansing fluid is poured from the electromagnetic valve unit 3, whereby the distal surface of the observation lens 20 is cleansed or a body cavity is aerated.

In the distal part 16, the treatment appliance passage 46 is joined to the treatment appliance insertion hole 21. When the pumps in the electromagnetic valve unit 3 are actuated, an intracavitary juice or the like can be sucked through the treatment appliance insertion hole 21. A treatment appliance inlet 47 is bored in a branch of the bifurcation member 45 other than the branch thereof from which the suction tube 14 is led out. An operator inserts a treatment appliance into the treatment appliance passage 46 through the treatment appliance inlet 47.

The built-in components, that is, the light guide 28, driving and image transmitting cable 29, aeration/perfusion channel 44, and treatment appliance passage 46 are integrated into a protective tube 48. The protective tube 48 is passed through a hole bored nearly in the center of the base 34 along the longitudinal axis thereof (the axis of the hole runs parallel to the longitudinal axis of the base 34).

As shown in FIG. 2A, the proximal unit 12 is shaped symmetrically with respect to a center axis thereof that is nearly aligned with the axis of insertion of the insertion unit 11. More particularly, the proximal unit 12 is shaped substantially like a cylinder of rotation symmetry with respect to the center axis. The base 34 is located near the center axis of the proximal unit 12. As mentioned above, the motors 35a and 35b and others are mounted symmetrically to each other on the face and back of the base 34. Moreover, the center of gravity of the entire proximal unit 12 lies near the center axis of the proximal unit 12.

Moreover, the treatment appliance inlet 47 is disposed so that the center axis thereof will be nearly aligned with the center axis of the proximal unit 12. The portion of the treatment appliance inlet 47 near the opening thereof is formed with a soft tube or a flexible pipe that can be bend with an extraneous force. The treatment appliance inlet 47 can be freely bent as indicated with alternate long and two short dashes lines in FIG. 4.

Figure 5:
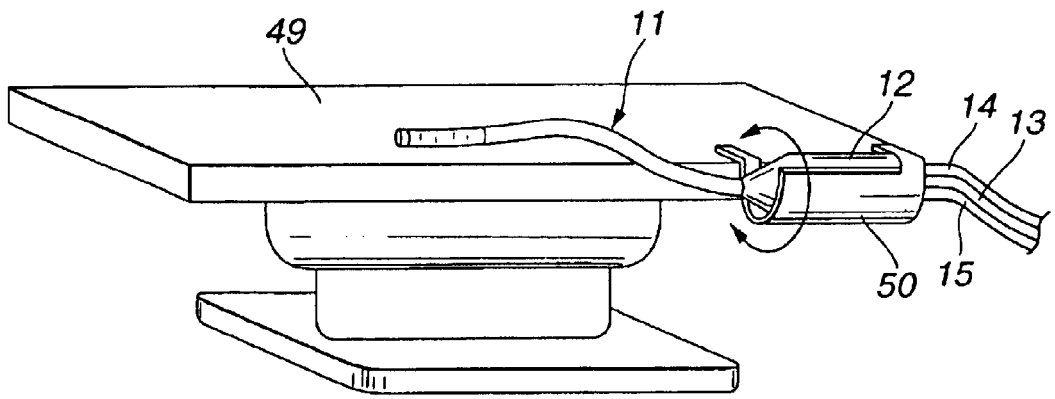

FIG. 5 shows a major portion of a combination of the video endoscope system 1 including the present embodiment and an operating table 49.

An endoscope holder 50 shaped like a truncated cylinder whose inner diameter is slightly larger than the outer diameter of the proximal unit 12 is fixed to an edge of the operating table 49 near a corner thereof. The endoscope holder 50 is designed so that the video endoscope 2 can be put in the endoscope holder 50 with the center axis of the proximal unit 12 thereof nearly aligned with the center axis of the endoscope holder 50.

As seen from FIG. 5, the power cable 15 is led out while being substantially aligned with the axis of insertion of the insertion unit 11. In other words, power is delivered to the motor unit 24 and the communication device 31 that drives the CCD 55 over the power cable 15. The lamp 25 in the light source unit 23 is, as shown in FIG. 2A, driven with the battery 26. Power may be delivered to the light source unit 23 from the driving power supply unit 7 over the power cab.

Since the power cable 15 is substantially aligned with the axis of insertion of the insertion unit 11, when the insertion unit 11 is twisted, the power cable 15 will not be rotated eccentrically but will be twisted accordingly. This feature has the merit that the power cable 15 will not block the space in which an operator moves.

Moreover, the aeration/perfusion tube 13 and suction tube 14 are led out from the proximal unit 12 while being substantially aligned with the axis of insertion of the insertion unit 11.

Consequently, since the tubes 13 and 14 over which a fluid is fed or sucked are substantially aligned with the axis of insertion of the insertion unit 11, when the insertion unit is twisted, the tubes 13 and 14 will not be rotated eccentrically but will be twisted accordingly. The tubes will therefore not block the space in which an operator moves.

Moreover, since the tubes 13 and 14 are soft, they will hardly resist the rotation of the proximal unit 12 interlocked with the twist of the insertion unit 11. The insertion unit 11 can be twisted easily.

According to the present embodiment, the driving power supply unit 7 from which driving power is delivered to the motors 35a and 35b need not be separated from the endoscope 2. The power supply of the video processor 6 may be used in common. Otherwise, a battery may be incorporated in the proximal unit 12 instead of employment of the driving power supply unit 7. As for the battery 26, the driving power supply unit 7 may be used on behalf of the battery 26. Otherwise, the power supply of the video processor 6 may be used in common and substituted for the battery 26.

Figure 6A:
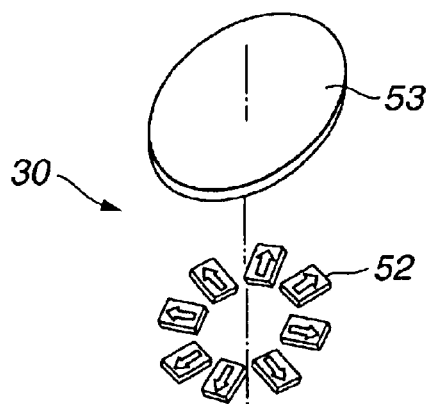
FIG. 6A shows an operation unit with an angling member thereof removed.
Figure 6B:
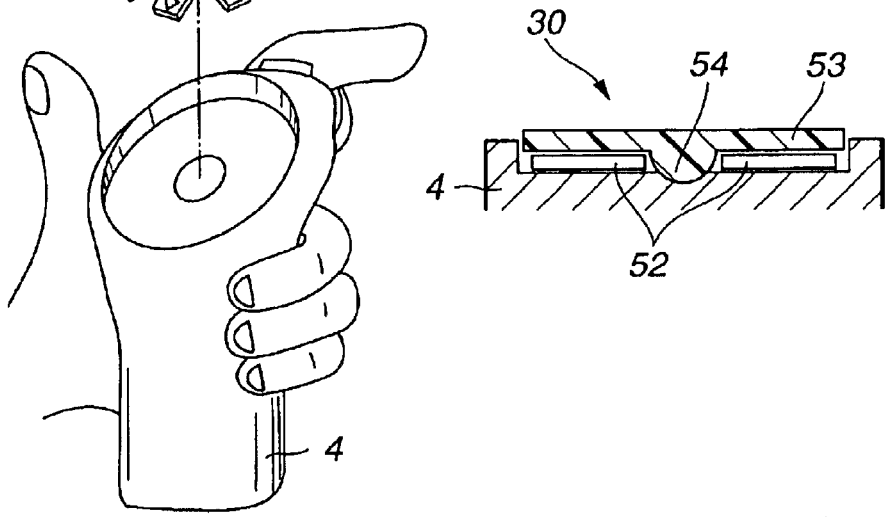
FIG. 6B shows the internal structure of the angling member.
Figure 6C:
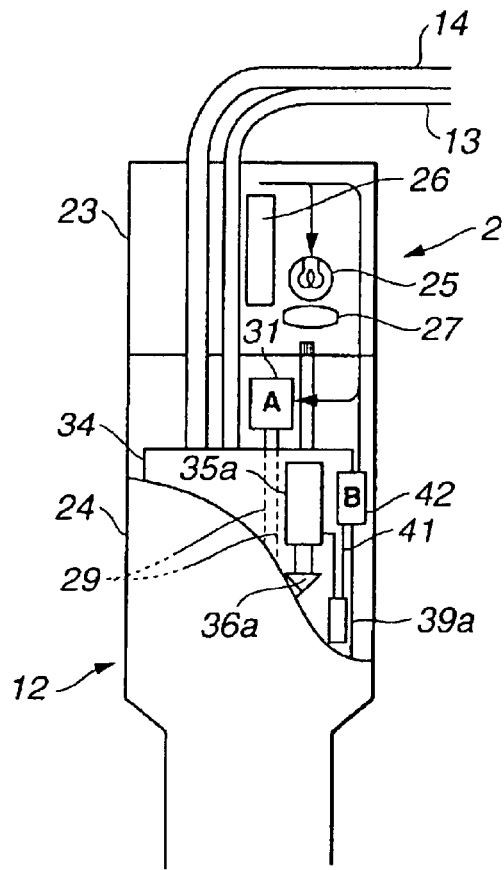
FIG. 6C shows a major portion of the proximal unit of a video endoscope.

For example, as shown in FIG. 6C, the battery 26 incorporated in the proximal unit 12 may be used to drive the lamp 25 in the light source unit 23, the motor unit 24, CCD 55, and communication device 31 respectively.

±Referring to FIG. 6C, power developed by the battery 26 is delivered to the lamp 25 and also delivered to the communication device 31 that drives the CCD 55 and the motor control circuit 39a that controls driving of the motor 35a. The power developed by the battery 26 is also delivered to the motor control circuit 39b that is not shown in FIG. 6C.

When the components are arranged as mentioned above, the power cable 15 need not be led out of the endoscope 2. Only the tubes over which a fluid is sucked or fed are led out of the rear end of the proximal unit 12. This feature provides the merit that the power cable will not interfere with an operator.

The operation unit 4 has an angling member 30, which will be described in conjunction with FIG. 6A, disposed on the top thereof. Aside from the angling member 30, a switch 4a used to control the electromagnetic valve unit 3 and a switch 4b used to give a freeze instruction or the like to the video processor 5 are located on the top of the operation unit 4. An instruction signal produced responsively to the press of the switch is transferred to the control circuit 5A included in the scope interface unit 5 over the operation unit connection cable 10.

The control circuit 5A is connected to the communication device 43 and also connected to the electromagnetic valve unit 3 and the video signal production circuit 6B included in the video processor 6 over a cable. When the angling member 30 is manipulated, an instruction signal produced responsively to the manipulation is transferred to the communication device 42 via the communication device 43.

Moreover, when the switch 4a is pressed, aeration, perfusion, or suction to be performed by the electromagnetic valve unit 3 is controlled. When the switch 4b is pressed, freezing is controlled.

As shown in FIG. 2A and FIG. 2B, the operation unit 4 is connected to the scope interface unit 5 over the operation unit connection cable 10. A pair of communication devices may be included in the scope interface unit 5 and operation unit 4 respectively so that the scope interface unit and operation unit can communicate with each other by radio.

Figure 6D:
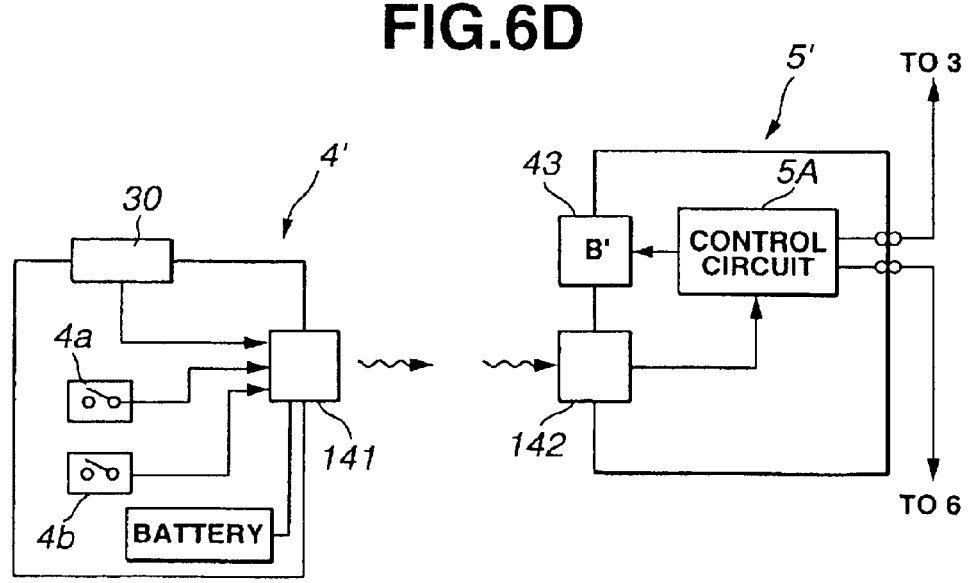
FIG. 6D is a block diagram schematically showing the electric configurations of the operation unit and a scope interface.

Specifically, the scope interface unit and operation unit may have the configurations like those shown in FIG. 6D. An operation unit 4' shown in FIG. 6D does not, unlike the operation unit 4 shown in FIG. 2B, have the operation unit connection cable 10 but includes the angling member 30, the switches 4a and 4b, and a communication device 141. The communication device 141 is powered by a battery 143.

On the other hand, a scope interface unit 5' shown in FIG. 6D has, in addition to the same components as the scope interface unit 5 shown in FIG. 2B, a communication device 142 that receives a signal from the communication device 141 by radio. A signal received by the communication device 142 is transferred to the control circuit 5A.

As shown in FIG. 2A and others, for example, the communication device 43 is used to communicate with the communication device 42. Moreover, a wireless operation unit 9 may be included (in addition to the wired operation unit 4). An instruction signal of a radio wave may be transmitted to the communication device 43 via a communication device, which is not shown, included in the operation unit 9, whereby required control may be extended.

FIG. 6A is an enlarged view of the operation unit 4 with the angling member 30 removed. The operation unit 4 has a concave part formed in the top thereof. A plurality of switches 52 is put in the concave part, and covered with an upper cover 53. Thus, the angling member 30 is constructed.

To be more specific, eight switches 52 are placed equidistantly in a circumferential direction in the concave part. A command output indicating an upward direction, a downward direction, a leftward direction, a rightward direction, a left upward direction, a left downward direction, a right upward direction, or a right downward direction can be produced as a direction of angling.

Each switch 52 is structured so that when the upper surface thereof is pressed, an electrical contact is closed to produce an output. Furthermore, the upper surfaces of the switches 52 are covered with the upper cover 53 having elasticity, such as, an upper cover made of a rubber.

FIG. 6B is a sectional view showing the upper cover 53 and switches 52. The upper cover 53 is shaped like a disk and has a hemispheric projection 54 formed in the center of the back thereof. The upper cover 53 is structured to be able to tilt in every direction with the hemispheric projection 54 as a fulcrum.

Operations to be exerted by the present embodiment having the foregoing components will be described below.

According to the present embodiment, the aeration/perfusion tube 13 and suction tube 14 led out of the video endoscope 2 are routed to the electromagnetic valve unit 3. Moreover, the power cable 15 is routed to the driving power supply unit 7. Thus, the connected state shown in FIG. 2A is attained. In this state, when the power supply of the video processor 6 is turned on, endoscopic examination can be performed.

An operator may hold the proximal unit 12 of the video endoscope 2. Otherwise, as shown in FIG. 5, the proximal unit 12 of the video endoscope 2 is held in the endoscope holder 50. The insertion unit 11 is then inserted into a patient who is not shown, whereby endoscopic examination can be started.

According to the present embodiment, the light guide 28 over which illumination light is propagated and the driving and image transmitting cable 29 over which the CCD is driven or an image is transmitted are passed through the insertion unit 11 and proximal unit 12 alike. However, a universal cord containing the light guide 28 and driving and image transmitting cable 29 is not led out of the proximal unit 12.

In other words, as mentioned above, a light source means such as the lamp 25 is incorporated in the proximal unit 12. This obviates the necessity of connecting the endoscope to an external light source apparatus.

Moreover, driving of the CCD and transmission of image data are performed by radio between the communication devices 31 and 32. Therefore, the driving and image transmitting cable 29 need not be led out of the proximal unit 12 and routed to the video processor 6.

For the purpose of endoscopic examination, an operator may want to insert the insertion unit 11 smoothly into the tortuous lumen of a body cavity. In this case, preferably, the distal portion of the insertion unit 11 is angled in conformity with the lumen of the body cavity.

In such a case, an operator holds the operation unit 4 connected to the scope interface unit 5 over the operation unit connection cable 10. The operator then presses the switch 52 that is included in the angling member 30 formed on the top of the operation unit and that indicates a direction in which the operator wants to angle the insertion unit. Consequently, an angling instruction signal is produced.

The signal is transferred to the scope interface unit 5. Thereafter, the communication device 43 transmits the signal by radio. The communication device 42 included in the proximal unit 2 receives the signal of a radio wave. The motor control circuits 39a and 39b produce control signals according to the instruction signal, and thus control the rotations of the motors 35a and 35b respectively. Consequently, the bending section 17 can be bent in a desired direction.

As mentioned above, the operation unit 4 is separated from the video endoscope 2. The proximal unit 12 need not be held all the time in order to transmit an angling instruction. This leads to improved maneuverability for angling.

Moreover, as shown in FIG. 2A, the aeration/perfusion tube 13 and suction tube 14 led out of the electromagnetic valve unit 3 and the power cable 15 led out of the driving power supply unit 7 that drives the motors 35a and 35b should be routed to the proximal unit 12.

The light guide 28 and driving and image transmitting cable 29 that are fragile are not led out of the proximal unit 12. Therefore, a universal cord on which a heavy torsion is likely to be applied is excluded. Such a drawback can therefore be overcome that when an endoscope is angled, a universal cord moves and interferes with an operator. This leads to greatly improved maneuverability or use-friendliness.

Moreover, the inclusion of the motors 35a and 35b in the proximal unit 12 obviates the necessity of leading out a universal cord. Compared with a case where a universal cord is led out, a driving force can be effectively utilized in pulling the angling wires 40a and 40b. Consequently, a motor exerting a small driving force may be adopted as the motors 35a and 35b. This leads to energy saving and a compact and lightweight design.

As mentioned above, the driving power supply unit 7 may be replaced with the battery 26 that is incorporated in the proximal unit 12. In this case, the number of connections can be decreased. No universal cord is led out of the proximal unit 12. Moreover, the proximal unit 12 is shaped like a cylinder that is nearly coaxial to the insertion unit 11. Therefore, when an operator twists the insertion unit 11, the proximal unit 12 rotates but does not resist the twisting. Consequently, the operator can twist the insertion unit 11 easily with a light force.

Moreover, the center of gravity of the proximal unit 12 is located near the axis of insertion of the video endoscope 2. The proximal unit 12 hardly generates a torque. Therefore, only a small force is needed to twist the insertion unit 3. This contributes to lightening of operator's fatigue.

Now, the axis of insertion of the video endoscope 2 refers to an axis of symmetry of the shape of the insertion unit 11 that is tubular and symmetrical with respect to an axis.

Moreover, the center of gravity of the proximal unit 12 may not lie on the axis of insertion but may lie at a position deviated from the axis of insertion in a downward direction of angling. At this time, when the proximal unit 12 balances with gravity, the proximal unit 12 acts as a rotor. Moreover, the upward direction of angling for the insertion unit 11 corresponds to an upward vertical direction in a normal coordinate system (herein, an absolute coordinate system) outside a human body in which gravity acts.

Figure 6E:
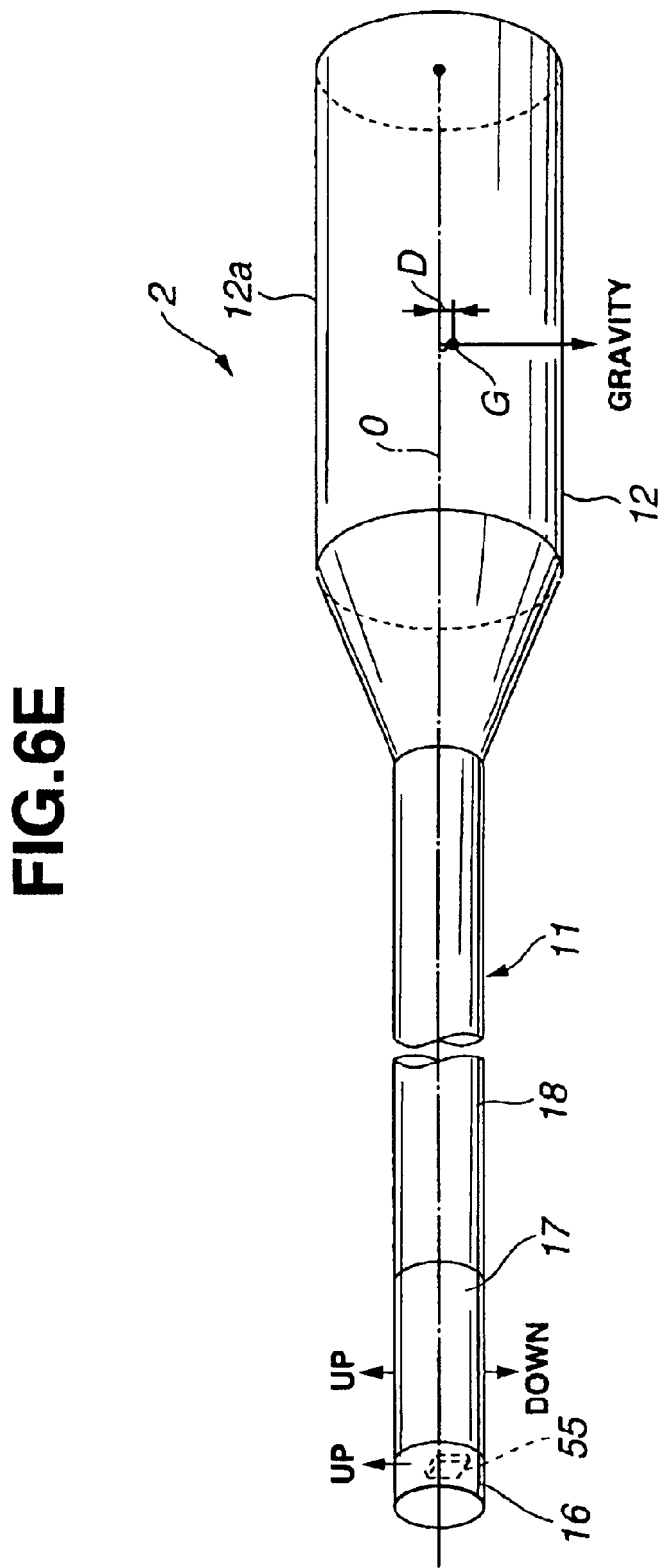

FIG. 6E depicts the above description. As shown in FIG. 6E, when the insertion unit 11 is held straight, the center axis o thereof passes the center of the proximal unit 12 shaped like a cylinder. Since the proximal unit 12 has built-in components, the position of the center of gravity G of the proximal unit 12 lies on the center axis O. When the bending section 17 is bent upwards or downwards with respect to the center axis O, the center of gravity is slightly displaced in the downward direction. Referring to FIG. 6E, D denotes the distance between the center axis o and the center of gravity G.

Consequently, when no force acts on the insertion unit 11, the state shown in FIG. 6E is attained. When a state different from the state is attained, a force acts to restore the state shown in FIG. 6E. In other words, when gravity acts as shown in FIG. 6E and the endoscope balances with the gravity, the highest point in the upward direction of angling in the bending section 17 is the uppermost position in the bending section. The point in the proximal unit 12 corresponding to the highest point is the uppermost position in the proximal unit 12. Reference numeral 12a denotes the uppermost position in the proximal unit 12.

In the state shown in FIG. 6E, the upward direction of angling to be designated at the time of bending the bending section 17 agrees with an upward vertical direction. Therefore, angling or the like can be achieved easily for the purpose of endoscopic examination. Incidentally, the upward direction of angling agrees with the upward direction of a displayed image that has been picked up by the CCD 55. In FIG. 6E, therefore, the upward direction of the CCD 55 is parallel to the upward direction of the bending section 17.

When the insertion unit 11 is twisted, the proximal unit 12 rotates. Consequently, a torque is applied to the insertion unit 11 so that the insertion unit 11 will balance itself, that is, the upward direction of angling of the insertion unit 11 will agree with a vertical direction. Therefore, when an operator alleviates a torsion, the insertion unit 11 autonomously returns to the balanced state. Consequently, the upward direction of angling agrees with the vertical direction. In particular, when the insertion unit is inserted into the large intestine, since the lumen of the large intestine is complexly tortuous, if an operator becomes aware of the shape of the lumen, the operation will be able to insert the insertion unit easily.

An operator may try to roughly grasp the current shape of a lumen from a patient's posture and the shape of the bending section 17 bent in the absolute reference frame. When the insertion unit 11 is twisted, if the operator changes the way of holding the insertion unit, the operator cannot recognize any longer to what direction in the absolute reference frame the upward direction of angling of the insertion unit 11 lying in the patient body corresponds. However, when the insertion unit 11 held by an operator is released, the proximal unit 12 autonomously returns to the balanced state so that the upward direction of angling will agree with the upward vertical direction in the absolute reference frame. The operator can recognize to what direction in the absolute reference frame the upward direction of angling of the insertion unit 11, that is, of the bending section 17 corresponds. Consequently, the operator easily grasps the shape of a lumen.

Moreover, when an operator perceives a torque exerted when the insertion unit 11 returns to the balanced state, that is, attempts to face in the upward vertical direction, the operator can learn to which of vertical directions the upward direction of angling corresponds, and can roughly grasp in what direction in the absolute reference frame the insertion unit 11 is oriented currently. In other words, the operator can easily recognize the relationship between the upward direction of the bending section 17 and the upward direction in the absolute coordinate system.

Moreover, the motors 35a and 35b are used to pull the angling wires 40a and angling wires 40b in order to angle the insertion unit. An operator should merely turn on or off electric switches, which are used to control the motors 35a and 35b, by manipulating the operation unit 4. The operation unit 4 need not be connected to the proximal unit 12 on a fixed basis. An operator can therefore manipulate the operation unit 4 and insertion unit 11 using his/her both hands.

According to the related art, as shown in FIG. 1, when the insertion unit 129 is twisted, the operation unit 130 is twisted accordingly. In order to twist the operation unit 130, an operator must twist, for example, his/her wrist and press a switch or turn the angling knob 137 at the same time. Thus, the operator finds it complex to operate the endoscope.

Moreover, in order to turn the angling knob 137, a force strong enough to bend the bending section 135 is needed.

In contrast, according to the present embodiment, since the operation unit 4 is separated from the insertion unit 11, the operation unit 4 can be held in any operator's intended direction irrespective of the state of the insertion unit 11. Moreover, the insertion unit is angled using electrical driving forces exerted by the motors 35a and 35b. An operator should merely turn on or off electric switches but need not exert a strong force. It is therefore easy to operate the endoscope.

The aeration/perfusion tube 13 and suction tube 14 that are connections are not sheathed with a universal cord. If the tube is damaged, it can be repaired or replaced with a new one. Moreover, since the tubes alone are led out of the endoscope, the tubes may be disposable.

Angling to be achieved using the operation unit 4 will be described below.

When a plurality of switches is included, an operator must discern the position of an intended switch so as to press the correct switch. When the operator gets accustomed to operation of the endoscope in some degree, the operator may sensuously recognize the arrangement of the switches. Even in this case, if the switches are independent of one another, an incorrect switch may be pressed.

According to the present embodiment, as shown in FIG. 6A and FIG. 6B, the one upper cover 53 is tilted in order to press the switch 52 located below. An incorrect switch will hardly be pressed.

The mutually independent switches 52 may not be covered with the upper cover 53. For example, a pressure-sensitive element that senses a pressure applied in a direction in which a pressed switch lies may be employed. In this case, an operator's input can be detected as an indication of not only one of eight directions but also an obliquely left upward direction of 11° and others. Thus, the operator's input can be converted into an electric signal according to a resolution offered by the pressure-sensitive element. However, when the operator wants to enter a delicate direction, for example, the obliquely left upward direction of 11° continuously, it is hard to enter the direction continuously. The endoscope cannot be angled exactly in that direction and can be hardly advanced in the intended direction. Even when the direction of the endoscope must be corrected during advancement, it is hard to enter a direction in which the endoscope must be returned. Therefore, there is difficulty in changing the direction of the endoscope.

According to the present embodiment, the input means used to enter eight directions or sixteen directions is covered with the upper cover 53 that can be tilted in all directions. An operator can enter any direction, and an output is limited to any of the eight or sixteen directions. Therefore, even if an operator enters a direction indistinctly, an output indicates the direction. An operator need not make a correction from time to time but can easily predict a direction in which the endoscope advances from the current position. Thus, the endoscope is easy to operate.

Consequently, a direction can be entered easily, and an output is limited to specific directions. An indistinct entry of a direction will not affect an output. This leads to improved maneuverability for angling.

The present embodiment provides advantages described below.

A universal cord used to connect the endoscope to the external video processor 6 and light source apparatus need not be led out of the proximal unit 12. Even when the insertion unit 11 must be twisted during insertion work, the insertion unit 11 can be easily twisted. Consequently, the insertion work can be achieved readily. This leads to improved maneuverability.

Moreover, the operation unit 4 may be composed of electric switches alone. Nevertheless, the angling wires can be pulled. The operation unit 4 can be separated from the insertion unit 11 and can be manipulated easily.

Moreover, the motors 35a and 35b serving as an actuator are included in the proximal unit 12. Friction of a traction member occurs within the insertion unit 11 alone. (If the universal cord is included, friction occurring within the universal cord works.) A motor providing only small power may be adopted as the motors 35a and 35b. This leads to a compact endoscope.

Second Embodiment

Next, a second embodiment of the present invention will be described with reference to FIG. 7. The present embodiment includes the same components as the first embodiment. In addition, tension detecting means are included for detecting the tensions of the angling wires 40a and 40b. The outputs of the tension detecting means are analyzed so that the endoscope can be inserted smoothly into a tortuous lumen or the like.

A video endoscope 2' shown in FIG. 7 has the same components as the video endoscope 2 of the first embodiment. In addition, tension sensors 56a and 56a' for detecting the tensions of two angling wires 40a and 40a' lying through the insertion unit 11 are disposed in the middles of the angling wires.

The tension sensors 56a and 56a' detect the tensions of the angling wires 40a and 40a'. The outputs of the tension sensors 56a and 56a' are transferred to a control CPU 57 (included in the motor control circuit 39a).

The tips of the angling wires 40a and 40a' are fixed to the bending section 17 that is the distal portion of the insertion unit 11. When the angling wire 40a or 40a' is pulled, the bending section 17 can be bent in the upward or downward direction.

Moreover, a pulley 38a about which the rear portions of the angling wires 40a and 40a' are wound has the rotation shaft thereof connected to the motor 35a. Thus, the pulley 38a is driven to rotate. In FIG. 7, for brevity's sake, the pulley 38a is driven to rotate while being connected directly to the motor 35a. Alternatively, as shown in FIG. 2A, the gears 36a and 37a may be interposed between the motor and pulley.

The rotation shaft of the pulley 38a is connected to an angle-of-rotation detector 58a such as a potentiometer, whereby an angle of rotation made by the pulley 38a can be detected. A magnitude of movement by which the angling wires 40a and 40a' have moved can be calculated from the angle of rotation made by the pulley 38a. An angle by which the bending section 17 is bent can be calculated from the magnitude of movement of the angling wires. A detection signal produced by the angle-of-rotation detector 58a is transferred to the CPU 57. The CPU 57 calculates the angle by which the bending section is bent.

FIG. 7 shows a bending section driving mechanism for driving the bending section in the upward or downward direction. Tension sensors 56b and 56b' and an angle-of-rotation detector 58b are included in a bending section driving mechanism for driving the bending section in the rightward or leftward direction. The outputs are transferred to the CPU 57. Herein, for brevity's sake, a description will be made in relation to angling in the upward or downward direction.

Moreover, the operation unit 4 (see FIG. 2A) further includes an automatic insertion support mode switch. When the switch is pressed, an instruction signal is transferred to the CPU 57. The CPU 57 controls the rotation of the motor 35a accordingly.

Next, operations to be exerted by the present invention will be described. The operations to be exerted by the components except the tension sensors 56a and 56a', angle-of-rotation detector 58a, and CPU 57 are identical to those of the first embodiment. Hereinafter, therefore, a description will be made of an operation to be exerted in an automatic insertion support mode attained by pressing the automatic insertion support switch included in the operation unit 4.

When the video endoscope 2' is inserted into a tortuous lumen, for example, the lumen of the large intestine, if the bending section 17 is kept thrust while being bent, the bending section merely pushes the tortuous lumen but does not advance. The bending section 17 is bent in conformity with the direction of the lumen in which the lumen advances naturally, and the distal part 16 is angled in the direction of the lumen. Thus, the video endoscope is thrust forwards and inserted.

As far as the electrically bendable endoscope 2' is concerned, a driving force exerted by, for example, the motor 35a is utilized in order to forcibly straighten the endoscope. Thus, the endoscope can be angled in conformity with the direction of a lumen. However, when the bending section 17 is straightened, the bending section deforms the lumen. The distal part 16 cannot therefore be angled in the natural direction of the lumen.

According to the present embodiment, the operation to be described below is exerted in the automatic insertion support mode. Therefore, the distal part 16 can be angled in conformity with the direction of a lumen without a deformation of the lumen.

For example, assume that when the insertion unit is angled in the downward direction, the operation unit 4 is manipulated to instruct angling in the opposite upward direction so that the insertion unit will be straightened.

When the insertion unit is angled in the downward direction, both the angling wire 40a for angling in the upward direction and the angling wire 40*a*' for angling in the downward direction are tensed. The tension of the angling wire 40*a*' for angling in the downward direction will be discussed below.

The operation unit 4 is manipulated in order to angle the insertion unit in a direction causing an angle, by which the bending section is bent, to decrease (from a state indicated with a solid line in FIG. 7 to a state indicated with an alternate long and two short dashes line). In this case, as long as neither the distal part 16 nor the bending section 17 comes into contact with a paries, the tension of the angling wire 40*a*' for angling in the downward direction decreases gradually along with a decrease in the angle by which the bending section is bent.

When the distal part 16 or bending section 17 comes into contact with a paries, an extraneous force is applied to the distal part or bending section. This causes the tension of the angling wire 40*a*' to increase. The instant the tension of the angling wire 40*a*' makes a transition from decrease to increase is the instant the distal part 16 or bending section 17 comes into contact with a paries.

The CPU 57 extends control so that the motor 35*a* will be kept driven until the instant the tension of the angling wire 40*a*' makes a transition from decrease to increase.

Consequently, the bending section 17 can be held straight until the instant it comes into contact with a paries. The distal part 16 can be angled in conformity with the direction of a running lumen without a deformation of the lumen.

An operator can easily grasp a direction in which the endoscope should be advanced. This leads to improved maneuverability.

The present embodiment provides advantages described below.

The bending section is kept straight until the instant it comes into contact with a paries. Consequently, the distal part can be angled in conformity with the direction of a lumen but not brought into contact with a paries. This leads to improved maneuverability. The other advantages are identical to those of the first embodiment.

Third Embodiment

Next, a third embodiment of the present invention will be described with reference to FIG. 8. The components of the present embodiment are partly different from those of the first embodiment.

A video endoscope 61 of the present embodiment shown in FIG. 8 has the insertion unit 11 and the proximal unit 12 proximal to the insertion unit. The treatment appliance inlet 47 is bored in the proximal unit 2 on a fixed basis. A connection cord 62 is led out of the rear end of the proximal unit 12. The connection cord 62 is routed to a motor case 63 (accommodating the motors 35*a* and 35*b*).

Similarly to the first embodiment (shown in FIG. 2A), the aeration/perfusion tube 13 and suction tube 14 that are routed to the electromagnetic valve unit 3, and the power cable 15 routed to the driving power supply unit 7 are led out of the motor case 63.

The video endoscope 61 includes the communication devices 31 and 42 shown in FIG. 2A, and can therefore transfer electric signals to or from the video processor 6 and scope interface unit 5 by radio.

According to the present embodiment, an operation unit connection cable 64 is branched out of the junction between the insertion unit 11 and proximal unit 12. The operation unit connection cable 64 terminates at the operation unit 4. In the present embodiment, when the angling member 30 of the operation unit 4 is manipulated, an instruction signal is transmitted to the motor control circuits 39*a* and 39*b* incorporated in the motor case 63 over signal lines that are contained in the operation unit connection cable 64, and the motors 35*a* and 35*b* are controlled.

When the operation unit 4 is manipulated, similarly to when the operation unit included in the first embodiment is manipulated, a signal is transferred to the communication device 43 included in the scope interface unit 5. The operation of the electromagnetic valve unit 3 is controlled via the scope interface unit 5. The other components are identical to those of the first embodiment.

Next, operations to be exerted by the present embodiment will be described below.

In the endoscope 122 of the related art (see FIG. 1), the operation unit 130 has the treatment appliance insertion port 140 on a fixed basis. For example, when an operator finds a lesion during a surgical procedure, he/she may want to use a treatment appliance. In this case, the operator holding the operation unit 130 inserts a treatment appliance into the distal part 134 of the endoscope 122 through the treatment appliance insertion port 140. Therefore, while the operator is inserting the treatment appliance, he/she cannot manipulate any other thing.

Moreover, if an operator wants to ask another operator or paramedic to insert a treatment appliance, since the treatment appliance insertion port 140 is bored in the operation unit 130, the operator holding the operation unit 130 must direct the treatment appliance insertion port 140 to the operator or paramedic who tries to insert the treatment appliance. Thus, the operator has to perform extra work other than operation of the endoscope 122. This restricts the operation of the endoscope 122.

A plurality of operators, that is, an operator who manipulates the operation unit 130 and an operator who manipulates a treatment appliance may work in cooperation for treatment. In this case, since the treatment appliance insertion port 140 is formed in the operation unit 130, the two operators must stand mutually closely to proceed with manipulations. The operators have their movements restricted and cannot smoothly proceed with the manipulations.

In contrast, according to the present embodiment, the treatment appliance inlet 47 is formed at an end of a unit other than the operation unit 4. The operation unit 4 can be distanced from the treatment appliance inlet 47. Therefore, a person who inserts a treatment appliance, and an operator who manipulates the treatment appliance will not interfere with the operator of the operation unit 4 but can treat the treatment appliance properly.

The present embodiment provides an advantage described below.

An operator who manipulates the operation unit 4 and an operator who manipulates a treatment appliance can proceed with manipulations while standing away from each other. This leads to improved maneuverability.

In FIG. 8, the motor case 63 is coupled to the connection cord 62 led out of the proximal unit 12. Alternatively, similarly to the first embodiment, the motor case may be included in the proximal unit 12. In this case, not only the foregoing advantage and the same advantages as those of the first embodiment are provided.

Fourth Embodiment

Figure 9:
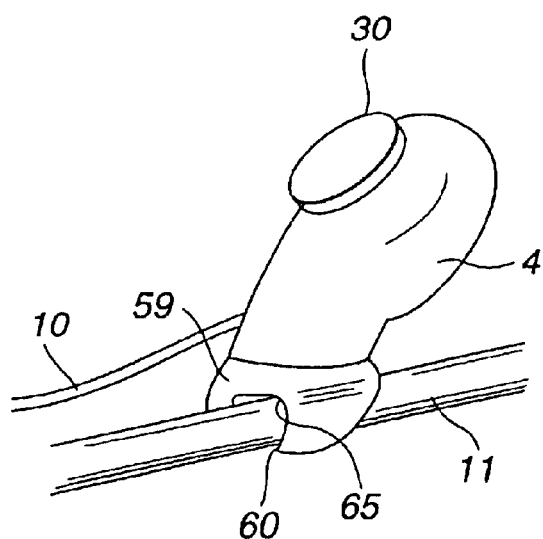
FIG. 9 shows an operation unit included in a fourth embodiment of the present invention and its surroundings.

Next, a fourth embodiment of the present invention will be described with reference to FIG. 9. FIG. 9 shows an operation unit of an endoscope in accordance with the fourth embodiment and its surroundings.

As described previously, the electrically bendable video endoscopes 2, 2', and 61 use the motor 35*a* or the like to bend the bending section 17. Herein, the operation unit 4 consists of electric switches that are used to issue a command to the motor 35*a* or the like. As shown in FIG. 2A, the operation unit 4 can be constructed independently of the endoscope 2.

According to the present embodiment, an insertion unit locking member 59 formed with an elastic member is fixed to, for example, the lower end of the operation unit 4. A hole 65 whose inner diameter is smaller than the outer diameter of the insertion unit 11 is formed in the insertion unit locking member 59. The hole 65 communicates with outside through an opening 60 formed in the lower end of the insertion unit locking member 59.

The width of the opening 60 and the inner diameter of the hole 65 are smaller than the outer diameter of the insertion unit 11. Since the insertion unit locking member 59 is formed with an elastic member, the insertion unit 11 can be pushed into the hole 65 formed in the insertion unit locking member 59 by widening the opening 60.

After the insertion unit 11 is fitted in the hole 65, since the inner diameter of the hole 65 is smaller than the outer diameter of the insertion unit 11 in a natural state, the operation unit 4 can be locked at any point on the insertion unit 11 owing to an elasticity. Incidentally, the operation unit connection cable 10 is led out of an area near the lower end of the operation unit 4. The other components are identical to those of the first embodiment.

Next, operations to be exerted by the present embodiment will be described below.

While holding the operation unit 4, an operator can insert the insertion unit 11 or manipulate the operation unit 4 to bend the bending section 17. During operation of the endoscope, an operator may have to insert, for example, forceps or operate the video processor 6. Otherwise, an operator may want not to hold the operation unit 4. In this case, the operator locks the operation unit 4 by mounting it on a point on the insertion unit 11 near the proximal end of the insertion unit 11 at which the operator can manipulate the operation unit 4 easily. Thus, the operator need not hold the operation unit 4. Nevertheless, when the operation unit must be manipulated, the operator can manipulate it in an easy-to-manipulate state.

In this case, when the insertion unit 11 is inserted, the point on the insertion unit on which the operation unit is mounted may shift. In this case, the operator can appropriately change the point on the insertion unit on which the operation unit is mounted.

According to the present embodiment, an operator mounts the operation unit 4 on a point on the insertion unit 11 at which the operator can easily manipulate the operation unit 4. The operator can manipulate the operation unit 4 without holding the operation unit 4 all the time.

Consequently, one hand with which the operation unit is held is freed and used to manipulate forceps or operate the video processor 6. This leads to improved maneuverability.

In the aforesaid embodiments, the video endoscope (electronic endoscope) has an imaging device incorporated in the distal part 16 thereof. The embodiments can be adapted to an optical endoscope devoid of the imaging device.

In this case, the driving and image transmitting cable 29 and communication device 31 included in the video endoscope 2 shown in FIG. 2A are not needed. Moreover, the external video processor 6 and monitor 8 are not needed in order to configure an endoscope system. Nevertheless, as described in relation to the first embodiment, the lamp 25 serving as a light source is incorporated in the proximal unit 12. A universal cord (or a light guide cable) over which the proximal unit 12 is connected to an external light source apparatus is not needed. The maneuverability of an endoscope during insertion thereof can be improved.

Figure 10:
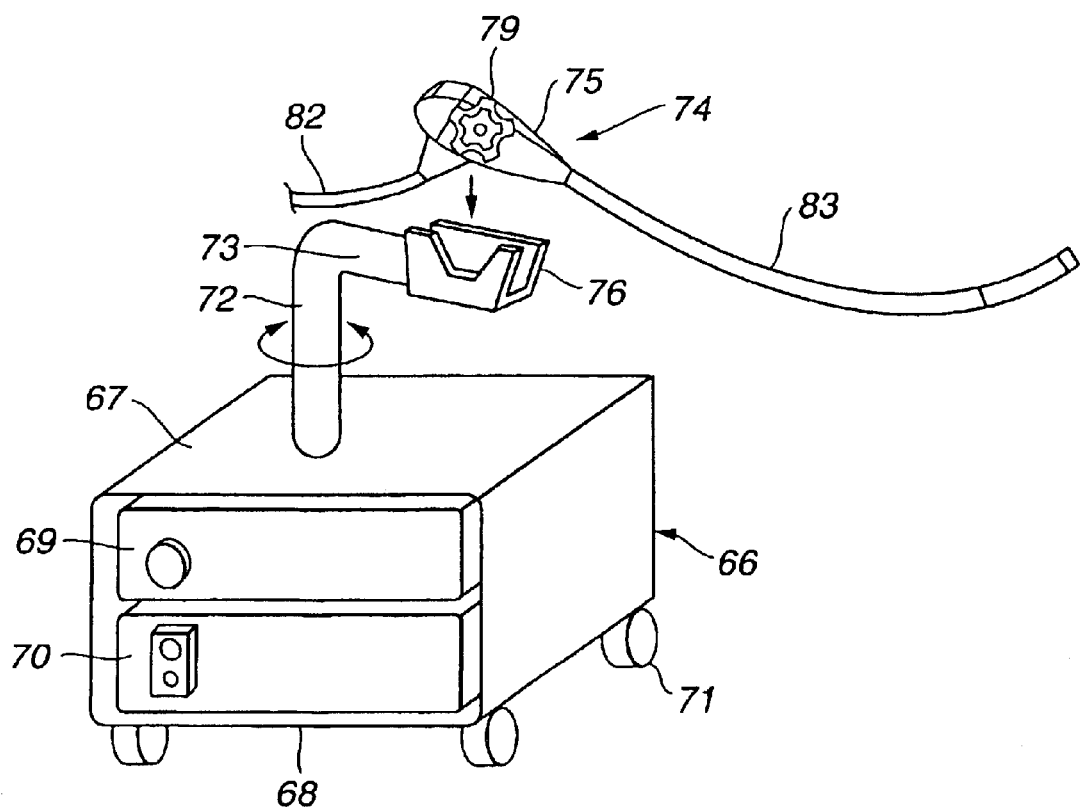
FIG. 10 shows the appearance of an endoscope cart having a support.
Figure 11:
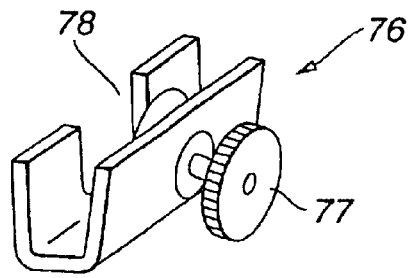
FIG. 11 shows a holder fixed to the tip of the support in enlargement.
Figure 12:
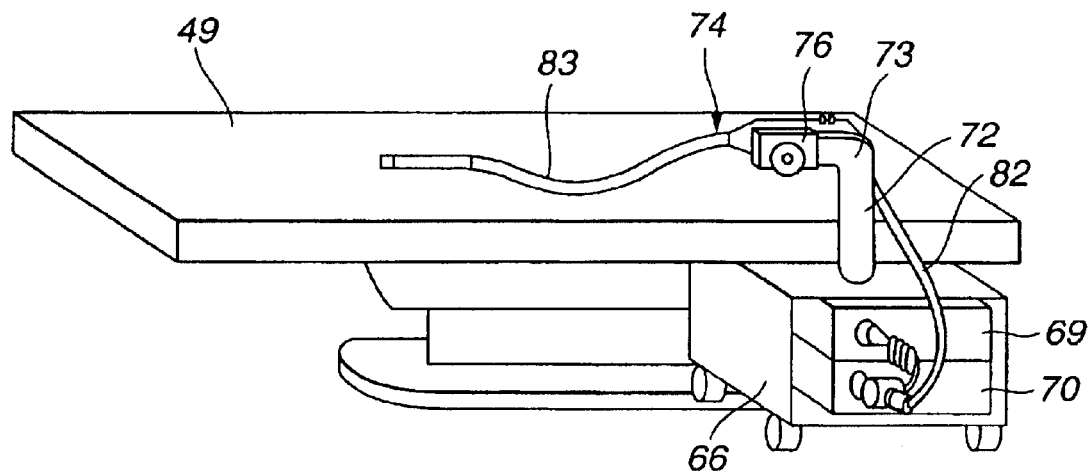
FIG. 12 shows a typical state in which preparations have been made for endoscopic examination with the endoscope cart placed under an operating table.

Referring to FIG. 10 to FIG. 12, an endoscope cart will be described below.

FIG. 10 shows an endoscope cart 66 into which an endoscope system is integrated. The endoscope cart 66 is shaped like a box. A space in which a video processor 69 and a light source apparatus 70 can be mounted is preserved between an upper panel 67 and a lower panel 68.

Four wheels 71 are fixed to the lower panel 68, whereby the endoscope cart 66 is entirely movable. The lower end of a support 72 that stands vertically is fixed to the upper panel 67. The support 72 has the upper part thereof bent horizontally, whereby a horizontal support portion 73 is formed.

The terminal part of the horizontal support portion 73 is formed as a holder 76 that can hold an operation unit 75 of an endoscope 74 and has a cross section shaped substantially like letter U.

As shown in FIG. 11, the holder 76 has a tightening member 77. When a knob of the tightening member 77 is turned, a disk-like member fixed to the end of the tightening member 77 advances or withdraws to tighten the holder. After the operation unit 75 is fitted in the holder 76, the holder is tightened. Thus, the operation unit 75 is prevented from coming off from the holder 76. Moreover, when the tightening member 77 is loosened, the operation unit 75 can be removed from the holder 76.

A notch 78 is formed in the flank of the holder 76. When the operation unit 75 is fitted in the holder 76, an angling knob 79 is exposed to outside through the notch 78. The angling knob 79 can be manipulated with the operation unit 75 held in the holder 76. The support 72 can rotate in horizontal directions with respect to the upper panel 67.

The height of the upper panel 67 is approximately 40 cm in practice and is, as shown in FIG. 12, limited to a level lower than the operating table 49. The endoscope cart can be placed under the operating table 49. The height of the horizontal support portion 73 is set to a value making the horizontal support portion 73 higher by approximately 40 cm than the operating table 49.

Next, operations to be exerted by the endoscope cart 66 will be described below.

Minimum necessary components of an ordinary video endoscope system include the video endoscope 74, video processor 69, and light source apparatus 70. The endoscope cart 66 in which the present embodiment is stored can accommodate the minimum necessary system components. Nevertheless, the height of the upper panel 67 is limited to a value equal to or smaller than the height of the operating table 49. Therefore, the endoscope cart 66 can entirely be placed under the operating table 49.

Incidentally, a monitor is necessary for endoscopic examination. The monitor is disposed at a position at which the monitor is opposed to an operator with the operating table 49 between them, so that the monitor can be easily seen by the operator.

Figure 13A:
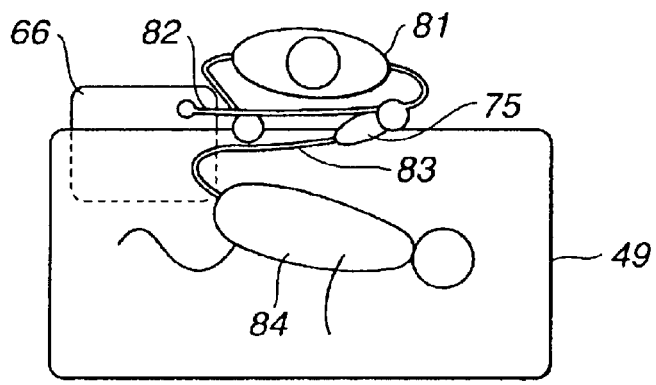
FIG. 13A is an explanatory diagram showing a case where endoscopic examination is performed with an endoscope system stored in the endoscope cart.
Figure 13B:
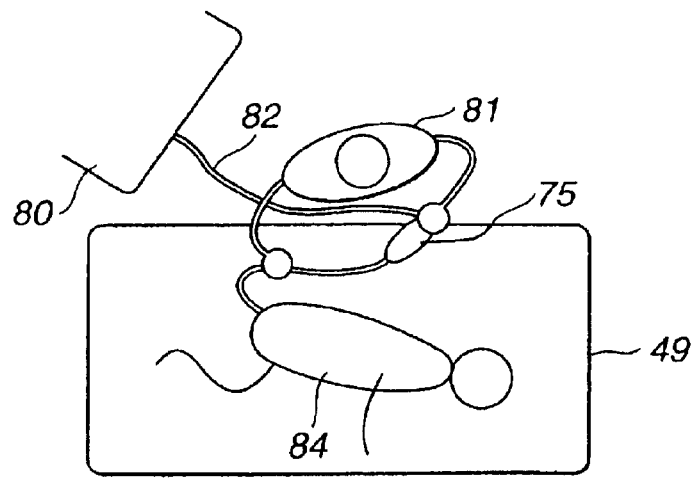
FIG. 13B is an explanatory diagram showing in comparison with FIG. 13A a case where endoscopic examination is performed using an endoscope cart included in a related art.

FIG. 13A shows the endoscope cart 66, in which the present embodiment is stored, placed under the operating table 49. FIG. 13B shows an endoscope cart 80 in accordance with a related art for comparison.

When the endoscope cart 80 of the related art is employed, since an operator 81 holds and manipulates the operation unit 75, a universal cord 82 cannot help lying between the operator 81 and operating table 49. Depending on the position at which the endoscope cart 80 is placed, the universal cord 82 lies by the side of the operator 81. Every time the operation unit 75 or an insertion unit 83 is twisted, the universal cord 82 is twisted in front of or by the side of the operator 81. The universal cord 82 may come into contact with the operator 81 or interfere with the operator 81.

In contrast, as shown in FIG. 13A and FIG. 12, according to the present embodiment, the endoscope cart 66 can be placed under the operating table 49, that is, at the operator's feet. The universal cord 82 will therefore not lie by the side of the operator 81. Although the universal cord 82 lies between the operator 81 and operating table 49, the universal cord 82 is not extended horizontally but routed vertically downwards to the endoscope card 66. The universal cord 82 will therefore not entwine the operator 81.

As shown in FIG. 12, the holder 76 is directed horizontally, and the support 72 can be turned horizontally. The endoscope 74 can therefore be turned horizontally while being held in the holder 76. When the endoscope 74 is inserted into a body cavity, the holder 76 is turned in a horizontal direction causing the proximal part of the insertion unit 83 to part from a patient 84. As the insertion progresses, the holder is turned so that the proximal part will approach the patient. Although the operation unit 75 is held in the endoscope cart 66 in a fixed basis, the insertion unit can be inserted without a problem.

The operation unit 75 itself is held in the holder 76. An operator need not bear the operation unit 75 and will therefore be little fatigued during a surgical procedure.

If the height of the support 72 of the endoscope cart 66 is made adjustable, the height can be changed according to the height of the operating table 49. This leads to improved maneuverability.

The endoscope cart 66 in which the present embodiment is stored provides an advantage described below.

Once the universal cord 82 is placed at the operator's feet, the universal cord 82 will little entwine the operator 81. This leads to improved maneuverability. Moreover, when the operation unit 75 is held on the endoscope cart 66, the operator's fatigue is alleviated.

Next, referring to FIG. 14, an endoscope having an insertion unit locking means will be described below.

Figure 14:
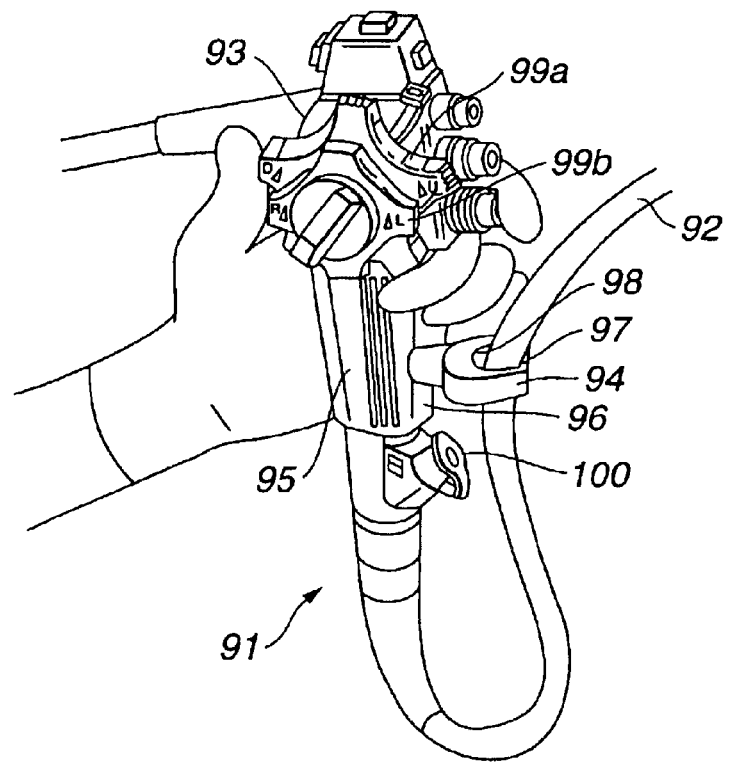
FIG. 14 shows an endoscope having a locking means for locking an insertion unit.

FIG. 14 shows an endoscope 91 having an insertion unit locking member 94 fixed to an operation unit 93 proximal to an insertion unit 92. The operation unit 93 is normally held with one hand of an operator. A grip 95 that is held by an operator and is formed as part of the operation unit 93 adjacently to the insertion unit 92 has a plurality of flat surfaces or curved surfaces.

The insertion unit locking member 94 formed with an elastic member that is deformed with an extraneous force is fixed to a back 96. The back 96 is a surface on a side of the grip opposite to a side thereof facing an operator's chest with the grip 95 of the operation unit 93 held by an operator.

The insertion unit locking member 94 has an opening 97 and a hole 98 that communicates with the opening 97. The width of the opening 97 and the inner diameter of the hole 98 are smaller than the outer diameter of the insertion unit 92. Since the insertion unit locking member 94 is formed with an elastic member, the insertion unit 92 can be fitted into the hole 98 formed in the insertion unit locking member 94 by widening the opening 97.

After the insertion unit 92 is fitted in the hole 98, since the inner diameter of the hole 98 is smaller than the outer diameter of the insertion unit 92 in a natural state, the insertion unit 92 can be locked owing to an elasticity.

A UD angling knob 99a that is used to angle the insertion unit in upward and downward directions, and an RL angling knob 99b that is used to angle the insertion unit in rightward and leftward directions are disposed on the right-hand flank of the operation unit 93 that is seen right by an operator. The directions of rotation in which the UD angling knob 99a can rotate are parallel to the upward and downward directions of angling. The UD angling knob 99a projects closely to an operator. When the UD angling knob 99a is rotated, the bending section of the insertion unit 92 bends in the upward direction. Herein, the upward direction of angling of the bending section refers to a direction of angling in which the bending section is seen bending in the upward direction of an endoscopic image. The upward direction of the bending section corresponds to a direction in which the back 96 of the operation unit 93 extends.

Next, operations to be exerted by the endoscope 91 will be described below.

Normally, in order to insert an endoscope, an operator manipulates the operation unit 93 with his/her right hand, and advances, withdraws, or twists the insertion unit 92 with his/her left hand. However, when an operator finds a lesion or the like and performs biopsy or treatment, the operator inserts a treatment appliance through a treatment appliance inlet 100. Therefore, the operator releases the insertion unit 92 temporarily so as to pick up the treatment appliance.

Moreover, in order to operate a video processor, the insertion unit 92 is released and a switch on the video processor is pressed. When the insertion unit 92 is released once, the insertion unit 92 moves. Consequently, the center of a field of view deviates from the lesion. Otherwise, the field of view loses the lesion. The endoscope must be focused on the lesion again.

According to the present embodiment, the insertion unit holder 94 is fixed to the back 96 of the operation unit 93. While a treatment appliance is being used, the insertion unit 92 is fitted and locked in the insertion unit locking member 94. In this state, the insertion unit 92 can be held with the right hand with which the operation unit 93 is held. Therefore, the insertion unit 92 will not move and a field of view will not deviate from a lesion. Moreover, the left hand that is freed can be used to manipulate the treatment appliance or operate the video processor.

The insertion unit locking member 94 is formed with an elastic member. The insertion unit 92 is pushed into the hole 98 by deforming the opening 97 of the insertion unit locking member 94. Consequently, the insertion unit 92 can be locked in the insertion unit locking member 94. When the insertion unit 92 is fitted in the insertion unit locking member 94, the hand with which the insertion unit 92 is held need not be parted from the insertion unit 92 but the insertion unit 92 can be readily locked.

The endoscope 91 provides an advantage described below.

Deviation of a field of view from a lesion, which occurs during manipulation of a treatment appliance or operation of a video processor, can be avoided. This leads to improved maneuverability.

Figure 15:
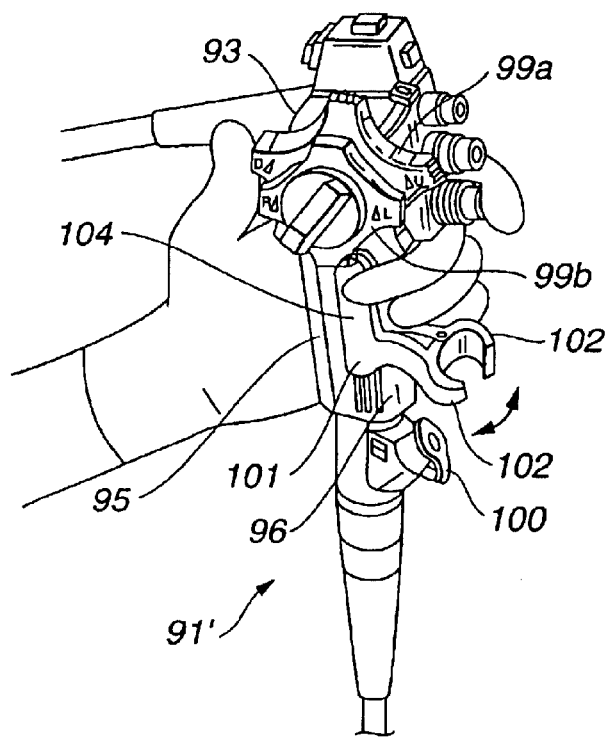
FIG. 15 shows an endoscope of an embodiment different from the endoscope shown in FIG. 14.
Figure 16:
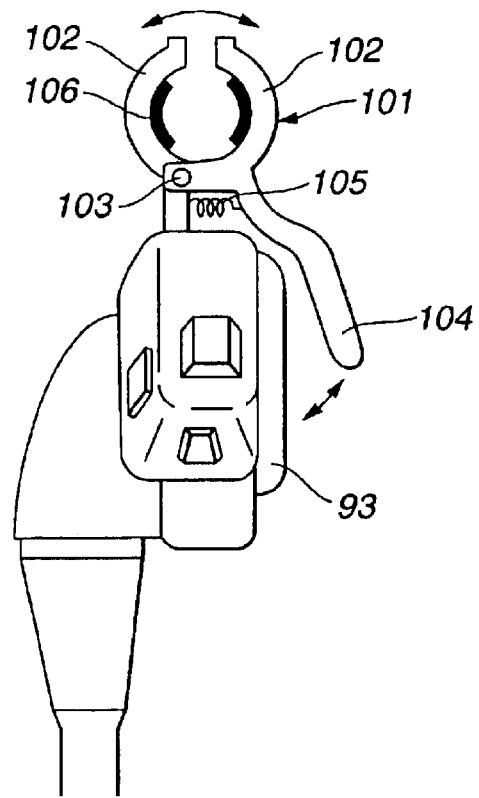
FIG. 16 is a schematic top view of the endoscope shown in FIG. 15.

Next, the components of a variant of the endoscope 91 shown in FIG. 14, that is, an endoscope 91' will be described below. FIG. 15 shows the appearance of the endoscope 91'. FIG. 16 is a plan view showing the endoscope 91' from above.

The endoscope 91' shown in FIG. 15 has an insertion unit locking member 101 fixed to the back 96 of the operation unit 93.

The insertion unit locking member 101 has two opening/closing members 102 joined with a pin 103 (see FIG. 16).

The opening/closing members 102 can pivot relatively to each other. Furthermore, one of the opening/closing members 102 has a lever 104 integrated therewith.

By manipulating the lever 104, the opening/closing members 102 can be opened or closed. As shown in FIG. 15, the lever 104 is elongated to have a longitudinal axis thereof extended in parallel to the grip 95. When an operator holds the grip 95 of the operation unit 93, the operator manipulates the lever 104 with his/her index finger, middle finger, or ring finger.

Furthermore, a spring 105 is attached to the opening/closing members 102. When the opening/closing members 102 open, the spring 104 exerts a force that constrains the opening/closing members to close. The inner diameter of a space defined by the opening/closing members 102 is smaller than the outer diameter of the insertion unit 92. Moreover, a frictional member 106 is bonded to the internal surfaces of the opening/closing members.

Next, operations-to be exerted by the endoscope 91' will be described below.

The lever 104 integrated with the opening/closing member 102 lies in parallel with the grip 95. Therefore, an operator can manipulate the lever 104 while holding the grip 95, and can thus open the opening/closing members 102.

The spring 105 that exerts a constraining force which constrains the opening/closing members 102 to close is attached to the opening/closing members 102. When an operator releases the lever 104, the opening/closing members 102 are readily closed.

Consequently, an operator readily opens or closes the insertion unit locking member 101 while holding the grip 95 of the operation unit 93 with his/her right hand. Moreover, the insertion unit 92 can be locked in the insertion unit locking member 101. The endoscope 91' provides the same advantage as the endoscope 91 shown in FIG. 14.

Namely, the endoscope 91' provides the advantage described below.

Deviation of a field of view from a lesion can be prevented from occurring during manipulation of forceps or operation of the video processor. This leads to improved maneuverability.

Next, an endoscope 111 shown in FIG. 17 will be described. The endoscope 111 is characterized by an operation unit 112 and a treatment appliance inlet 113.

Figure 17:
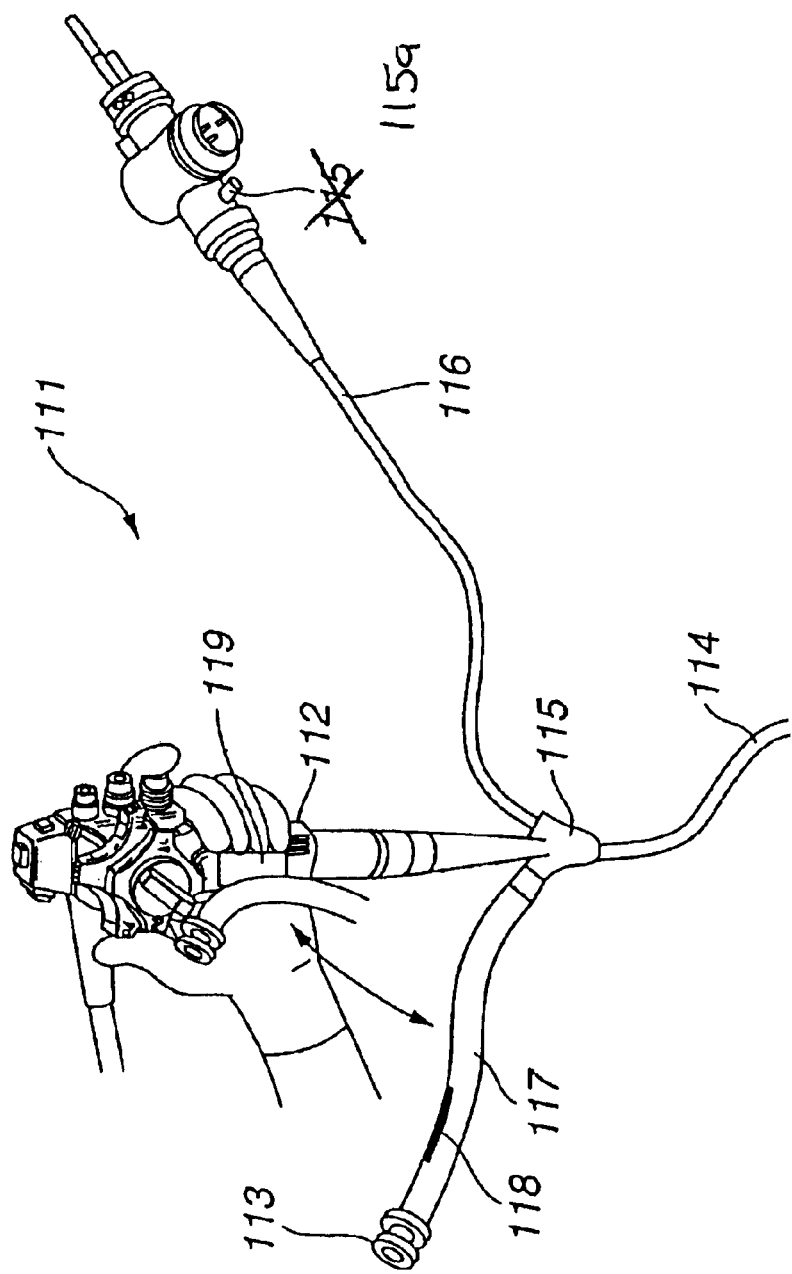
FIG. 17 shows an endoscope having a proximal unit of an insertion unit trisected to branch out an operation unit and others.

The endoscope 111 shown in FIG. 17 has a proximal unit 115 of an insertion unit 114 trisected into three branches. The operation unit 112 is connected to one branch, and the treatment appliance inlet 113 is connected to another branch. A scope connector 115a via which the endoscope is connected to a video processor and a light source apparatus is connected to the other branch over a universal cord 116.

The proximal unit 115 and treatment appliance inlet 113 are linked by a soft treatment appliance insertion tube 117. The treatment appliance inlet 113 can be moved freely within the extent of deformation within which the treatment appliance insertion tube 117 can be deformed.

Moreover, a thin plate 118 made of an iron is mounted on the flank of the treatment appliance insertion tube 117. The thin plate 118 is attracted with a magnetic force exerted by a magnetic plate 119 that is fixed to the flank of the operation unit 112, whereby the treatment appliance insertion tube 117 is secured.

Next, operations to be exerted by the endoscope 111 will be described below.

In the endoscope 111, similarly to the endoscope 61 shown in, for example, FIG. 8, the operation unit 112 and treatment appliance inlet 113 can be separated from each other. An operator who manipulates the operation unit 112 and an operator who manipulates a treatment appliance can stand away from each other. The operators will not obstruct each other.

Moreover, the treatment appliance inlet 113 can be detachably attached to the operation unit 112 owing to a magnetic force. When the treatment appliance inlet 113 need not be moved, for example, when observation alone is carried out, the treatment appliance inlet 113 can be fixed to the operation unit 112. The treatment appliance inlet 113 will little interfere with an operator.

The endoscope 111 provides an advantage described below.

An operator who manipulates the operation unit 112 and an operator who manipulates a treatment appliance can proceed with manipulations while standing away from each other. This leads to improved maneuverability. The treatment appliance inlet 113 can be detachably attached to the operation unit 112. Therefore, when a treatment appliance is not used, the treatment appliance inlet 113 can be fixed to the operation unit 112. Consequently, the treatment appliance inlet 113 is prevented from obstructing an operator.

Incidentally, an embodiment constructed by combining parts of the aforesaid embodiments will also belong to the present invention.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope comprising:
  a main body comprising an insertion unit that has a bending mechanism and includes a freely bendable bending section, and a proximal unit disposed proximally to said insertion unit;
  an objective optical system mounted in an imaging window formed in a distal part of said insertion unit and a solid-state imaging device disposed at the position of the image plane of said objective optical system;
  an actuator, included in said proximal unit, for actuating said bending mechanism so as to bend said bending section;
  a light source unit, included in said proximal unit, for generating illumination light with which an object to be imaged by said solid-state imaging device is illuminated;
  a communication device, included in said proximal unit, for transmitting an image signal produced by said solid-state imaging device to an external signal processing unit by radio; and
  an operation unit separated from said main body and used to operate said actuator.

2. An endoscope according to claim 1, wherein:
  a scope interface unit receives an angling signal from said operation unit, produces an actuator driving signal, with which said actuator is driven, according to the angling signal, and transmits the actuator driving signal to said actuator; and
  the actuator driving signal sent from said scope interface unit is transmitted to said endoscope by radio.

3. An endoscope according to claim 2, wherein the angling signal sent from said operation unit is transmitted to said scope interface unit by radio.

4. An endoscope according to claim 1, wherein a driving power supply for delivering power to said light source unit, actuator, and solid-state imaging device. is included in said proximal unit.

5. An endoscope according to claim 1, wherein a motor that electrically rotates for driving is adopted as said actuator, and a driving power supply for delivering power to said light source unit, actuator, and solid-state imaging device is included in said proximal unit.

6. An endoscope according to claim 1, wherein a power cable which is routed to a driving power supply unit disposed outside said endoscope and over which driving power is delivered to said light source unit, actuator, and solid-state imaging device is led out of said endoscope while being aligned with the axis of insertion of said insertion unit.

7. An endoscope according to claim 1, wherein one or more fluid feeding channels that open upon the distal end of said bending section are included in said insertion unit, and connected to an electromagnetic valve unit, which controls feed or suction of a fluid over said fluid feeding channel and is disposed outside, by way of a plurality of soft tubes led out of said proximal unit.

8. An endoscope according to claim 7, wherein a fluid treating signal with which said electromagnetic valve unit is operated is transmitted by radio from said operation unit to said scope interface unit that controls said electromagnetic valve unit.

9. An endoscope according to claim 7, wherein said soft tubes are led out while being aligned with the axis of insertion of said insertion unit.

10. An endoscope according to claim 1, wherein said proximal unit disposed proximally to said insertion unit has an axis thereof nearly aligned with the axis of insertion of said insertion unit and has a shape that is substantially symmetrical with respect to the axis.

11. An endoscope according to claim 1, wherein the center of gravity of said proximal unit that is disposed proximally to said insertion unit and that contains built-in components is located on or near an extension of the axis of insertion of said insertion unit.

12. An endoscope according to claim 1, wherein when the center of gravity of said proximal unit that is disposed proximally to said insertion unit and that contains built-in components balances with gravity, the highest point in the upward direction in said bending section is an uppermost position in said bending section.

13. An endoscope according to claim 12, wherein when the center of gravity of said proximal unit that is disposed proximally to said insertion unit and that contains built-in components balances with gravity, the point in said proximal unit corresponding to the highest point in the upward direction in said bending section is an uppermost position in said proximal unit.

14. An endoscope according to claim 1, wherein the center of gravity of said proximal unit that is disposed proximally to said insertion unit and that contains built-in components deviates from the center axis of said proximal unit in a direction corresponding to a downward direction of angling that is designated in bending said bending section.

15. An endoscope according to claim 1, wherein said operation unit includes a locking means in which said insertion unit is locked while being permitted to be unlocked freely.

16. An endoscope according to claim 15, wherein when said insertion unit is fitted in said locking means, said insertion unit is locked owing to an elasticity exerted by a deformed elastic member.

17. An endoscope according to claim 15, wherein said locking member opens or closes with manipulation of an opening/closing lever and clamps said insertion unit.

18. An endoscope according to claim 17, wherein said opening/closing lever has an axis thereof extended substantially in parallel with the longitudinal axis of said operation unit, and said operation unit and said opening/closing lever can be held together with one hand.

19. An endoscope according to claim 1, wherein said signal processing unit processes an image signal produced by said solid-state imaging device so as to produce a standard video signal.

20. An endoscope system comprising:
an endoscope comprising:
a main endoscope body having a bending mechanism, and including an insertion unit that has a bending section capable of bending freely, and a proximal unit disposed proximally to said insertion unit;
an objective optical system mounted in an imaging window formed in the distal part of said insertion unit and a solid-state imaging device disposed at the position of the image plane of said objective optical system;
an actuator, included in said proximal unit, for actuating said bending mechanism so as to bend said bending section;
a light source unit, included in said proximal unit, for generating illumination light with which an object to be imaged by said solid-state imaging device is illuminated;
a communication device, included in said proximal unit, for transmitting an image signal produced by said solid-state imaging device to an external signal processing unit by radio; and
an operation unit separated from said main body and used to operate said actuator;
a signal processing unit for processing an image signal produced by said solid-state imaging device so as to produce a video signal;
a monitor on which an image picked up by said solid-state imaging device is displayed according to a video signal received from said signal processing unit; and
an actuator drive unit for producing a driving signal, with which said actuator is driven, according to an operation signal sent from said operation unit.

21. An endoscope according to claim 1, wherein the actuator bends the bending section by an electric motive power.

22. An endoscope according to claim 20, wherein the actuator bends the bending section by an electric motive power.

* * * * *